(12) United States Patent
Helekar et al.

(10) Patent No.: US 10,874,870 B2
(45) Date of Patent: Dec. 29, 2020

(54) METHOD AND APPARATUS FOR PROVIDING TRANSCRANIAL MAGNETIC STIMULATION (TMS) TO AN INDIVIDUAL

(71) Applicants: THE METHODIST HOSPITAL, Houston, TX (US); CORNELL UNIVERSITY, Ithaca, NY (US)

(72) Inventors: Santosh A. Helekar, Sugar Land, TX (US); Henning U. Voss, New York, NY (US)

(73) Assignees: THE METHODIST HOSPITAL, Houston, TX (US); CORNELL UNIVERSITY, Ithaca, NY (US)

(*) Notice: Subject to any disclaimer, the term of this patent is extended or adjusted under 35 U.S.C. 154(b) by 8 days.

(21) Appl. No.: 16/099,125

(22) PCT Filed: May 5, 2017

(86) PCT No.: PCT/US2017/031413
§ 371 (c)(1),
(2) Date: Nov. 5, 2018

(87) PCT Pub. No.: WO2017/193078
PCT Pub. Date: Nov. 9, 2017

(65) Prior Publication Data
US 2019/0209855 A1 Jul. 11, 2019

Related U.S. Application Data
(60) Provisional application No. 62/332,087, filed on May 5, 2016.

(51) Int. Cl.
*A61N 2/00* (2006.01)
*A61N 2/06* (2006.01)
(Continued)

(52) U.S. Cl.
CPC ............ *A61N 2/006* (2013.01); *A61B 5/0476* (2013.01); *A61B 5/05* (2013.01); *A61B 5/4836* (2013.01); *A61N 2/06* (2013.01); *A61N 2/12* (2013.01)

(58) Field of Classification Search
CPC ............. A61N 2/06; A61N 2/006; A61N 2/12
(Continued)

(56) References Cited

U.S. PATENT DOCUMENTS

| 4,537,198 A | 8/1985 | Corbett |
| 4,967,038 A | 10/1990 | Gevins |

(Continued)

FOREIGN PATENT DOCUMENTS

| CN | 2796743 Y | 7/2006 |
| CN | 105188844 A | 12/2015 |

(Continued)

OTHER PUBLICATIONS

Aleman, A., Use of Repetitive Transcranial Magnetic Stimulation for Treatment in Psychiatry, Clinical Psychopharmacology and Neuroscience, 2013, vol. 11, No. 2, pp. 53-59.
(Continued)

*Primary Examiner* — John P Lacyk
(74) *Attorney, Agent, or Firm* — Marshall, Gerstein & Borun LLP

(57) ABSTRACT

An apparatus for applying Transcranial Magnetic Stimulation (TMS) to the brain of an individual comprising: a head mount; a plurality of magnet assemblies for releasable mounting on the head mount; each of the magnet assemblies comprises a permanent magnet, and at least one of (i) a movement mechanism for moving the permanent magnet and/or (ii) a magnetic shield shutter mechanism, to provide a rapidly changing magnetic field; and a computerized controller for operating at least one of the movement mecha-
(Continued)

nism and the magnetic shield shutter mechanism of at least one of the magnet assemblies to apply a rapidly changing magnetic field to the brain of the individual, wherein the computerized controller is configured to provide one of intermittent oscillatory stimulation and continuous oscillatory stimulation, to induce weak electric currents in the brain of an individual so as to modify the natural electrical activity of the brain of the individual.

16 Claims, 18 Drawing Sheets

(51) Int. Cl.
*A61N 2/12* (2006.01)
*A61B 5/0476* (2006.01)
*A61B 5/05* (2006.01)
*A61B 5/00* (2006.01)

(58) Field of Classification Search
USPC .................................................. 600/9–15
See application file for complete search history.

(56) References Cited

U.S. PATENT DOCUMENTS

| | | | |
|---|---|---|---|
| 6,032,677 | A | 3/2000 | Blechman et al. |
| 6,123,657 | A | 9/2000 | Ishikawa et al. |
| 6,447,449 | B1 | 9/2002 | Fleischman et al. |
| 6,488,617 | B1 | 12/2002 | Katz |
| 7,013,177 | B1 | 3/2006 | Whitehurst |
| 8,560,073 | B2 | 10/2013 | Osorio |
| 8,888,672 | B2 | 11/2014 | Phillips et al. |
| 9,272,159 | B2 | 3/2016 | Phillips et al. |
| 9,456,784 | B2 | 10/2016 | Helekar et al. |
| 2002/0151760 | A1 | 10/2002 | Paturu |
| 2004/0193001 | A1 | 9/2004 | Miller |
| 2006/0015153 | A1 | 1/2006 | Gliner et al. |
| 2006/0094924 | A1 | 5/2006 | Riehl |
| 2006/0265022 | A1 | 11/2006 | John |
| 2007/0093706 | A1 | 4/2007 | Gevins |
| 2008/0014285 | A1 | 1/2008 | Di Mauro et al. |
| 2008/0312706 | A1 | 12/2008 | Zangen et al. |
| 2009/0082690 | A1 | 3/2009 | Phillips et al. |
| 2010/0185042 | A1 | 7/2010 | Schneider et al. |
| 2010/0210894 | A1 | 8/2010 | Pascual-Leone et al. |
| 2010/0249488 | A1 | 9/2010 | Kardos et al. |
| 2011/0015469 | A1 | 1/2011 | Walter et al. |
| 2011/0034822 | A1 | 2/2011 | Phillips et al. |
| 2011/0105826 | A1 | 5/2011 | Mishelevich et al. |
| 2011/0112427 | A1 | 5/2011 | Phillips et al. |
| 2011/0118536 | A1 | 5/2011 | Phillips et al. |
| 2011/0118636 | A1 | 5/2011 | Kitamura et al. |
| 2011/0184223 | A1 | 7/2011 | Peterchev et al. |
| 2011/0270345 | A1 | 11/2011 | Johnston et al. |
| 2012/0053449 | A1 | 3/2012 | Moses et al. |
| 2012/0157752 | A1 | 6/2012 | Nishikawa |
| 2013/0137918 | A1 | 5/2013 | Phillips et al. |
| 2014/0163305 | A1 | 6/2014 | Watterson |
| 2014/0179980 | A1 | 6/2014 | Phillips et al. |
| 2014/0200388 | A1 | 7/2014 | Schneider et al. |
| 2014/0276182 | A1 | 9/2014 | Helekar et al. |
| 2014/0276812 | A1 | 9/2014 | Batchelor et al. |
| 2016/0008620 | A1 | 1/2016 | Stubbeman |
| 2016/0193476 | A1 | 7/2016 | Helekar et al. |
| 2017/0136255 | A1 | 5/2017 | Helekar et al. |
| 2017/0224990 | A1 | 8/2017 | Goldwasser et al. |
| 2018/0350451 | A1 | 12/2018 | Ohnemus et al. |

FOREIGN PATENT DOCUMENTS

| | | |
|---|---|---|
| DE | 10 2011 050507 A1 | 11/2012 |
| EP | 2 968 968 A2 | 1/2016 |
| EP | 3 033 007 A4 | 5/2017 |
| WO | WO-2005/051306 A2 | 6/2005 |
| WO | WO-2009/033150 A1 | 3/2009 |
| WO | WO-2009/036040 A1 | 3/2009 |
| WO | WO-2010/025114 A1 | 3/2010 |
| WO | WO-2011/017466 A1 | 2/2011 |
| WO | WO-2012/126044 A1 | 9/2012 |
| WO | WO-2014/152827 A2 | 9/2014 |
| WO | WO-2015/023980 A2 | 2/2015 |
| WO | WO-2016/059556 A1 | 4/2016 |

OTHER PUBLICATIONS

Amassian, V. E et al., Transcranial Magnetic Stimulation in Study of the Visual Pathway, Journal of Clinical Neurophysiology, 1998, 15(4): 288-304.
Antal, A. et al., Electrical Stimulation and Visual Network Plasticity, Restorative Neurology and Neuroscience, 2011, vol. 29, pp. 365-374.
Azanon, E. et al., Somatosensory processing and body representation, Cortex 45, 2009, 1078-1084.
Beauchamp, M. S. et al., fMRI-Guided Transcranial Magnetic Stimulation Reveals That the Superior Temporal Sulcus is a Cortical Locus of the McGurk Effect,The Journal of Neuroscience, 2010, 30(7): 2414-7.
Beckers, G. et al., Cerebral visual motion blindness: transitory akinetopsia induced by transcranial magnetic stimulation of human area V5, Proceedings: Biological Sciences, 1992, 249(1325): 173-8.
Bikson, M. et al., Effects of Uniform Extracellular DC Electric Fields on Excitabiity in Rai Hippocampal Slices in Vitro, Journal of Physiology, 2004, vol. 557, pp. 175-190.
Buch, E. R. et al., Noninvasive Associative Plasticity Induction in a Corticocortical Pathway of the Human Brain, The Journal of Neuroscience, 2011, 31(48): 17669-79.
Cardenas-Morales, L. et al., Mechanisms and Applications of Theta-Burst rTMS on the Human Motor Cortex, Brain Topogr, 2010, Voi. 22, pp. 294-306.
Chen, R. et al., The Clinical Diagnostic Utility of Transcranial Magnetic Stimulation: Repost of an IFCN Committee, Clinical Neurophysiology, 2008, Voi. 119, pp. 504-532.
Dayan, Eran et al., Noninvasive brain stimulation: from physiology to network dynamics and back, Nature Neuroscience, Jul. 2013, vol. 16, No. 7.
De Pasquale et al., A Cortical Core for Dynamic Integration of Functional Networks in the Resting Human Brain, Neuron, 2012, 74(4): 753-64.
De Ridder, D. et al., Primary and Secondary Auditory Cortex Stimulation for Intractable Tinnitus, ORL, 2006, 68(1): 48-54.
Deans, J.K. et al,, Sensitivity of Coherent Oscillations in Rat Hippocampus to AC Electric Fields, Journal of Physiology, 2007, vol. 583, pp. 555-565.
Deco, G. et al., Ongoing Cortical Activity at Rest: Criticality, Multistability, and Ghost Attractors, The Journal of Neuroscience, 2012, 32(10): 3366-75.
Dell'Osso, B. et al., Meta-Review of Metanalytic Studies with Repetitive Transcranial Magnetic Stimulation (rTMS) for the Treatment of Major Depression, Clinical Practice & Epidemiology in Mental Health, 2011, 7, 167-77.
Delvendahl, I. et al., Plasticity of motor threshold and motor-evoked potential amplitude—A model of intrinsic and synaptic plasticity in human motor cortex?, Brain Stimulation 5, 2012, 586-593.
Devlin, J. T. et al., Stimulating language: insights from TMS, Brain, 2007, 130, 610-22.
Di Lazzaro, V. et al., Modulation of Motor Cortex Neuronal Networks by rTMS: Comparison of Local and Remote Effects of Six Different Protocols of Stimulation, Journal of Neurophysiology, 2011, vol. 105, pp. 2150-2156.
Esser, S.K. et al., Modeling the Effects of Transcranial Magnetic Stimulation on Cortical Circuits, Journal of Physiology, 2005, vol. 94, pp. 622-639.
Extended European Search Report for Application No. 14771163.4, dated Jan. 3, 2017.
Extended European Search Report for Application No. 14836452.4, dated May 2, 2017.

(56) References Cited

OTHER PUBLICATIONS

Farina, D. et al., Detecting the Unique representation of the Motor-Unit Action Potentials in the Surface Electromyogram, Journal of Neurophysiology, 2008, vol. 100, pp. 1223-1233.
First Office Action for Chinese Application No. 201480027788.3, dated Oct. 10, 2016.
First Office Action for Chinese Application No. 201480057016.4, dated May 28, 2018.
Fitzgerald, P. B. et al., GABA and cortical inhibition in motor and non-motor regions using combined TMS-EEG: A time analysis, Clinical Neurophysiology 120, 2009, 1706-1710.
Fox, M. D. et al., The human brain is intrinsically organized into dynamic, anticorrelated functional networks, Proceedings of the National Academy of Sciences of the USA, 2005, vol. 102, No. 27, 9673-8.
Fregni, F. et al., Technology Insight: NonInvasice Brain Stimulation in Neurology: Perspectives on the Therapeutic Potential of rTMS and tDCS, Nature Clinical Practice Neurology, 2007, vol. 3, pp. 1-11.
Frohlich, F. et al., Endogenous Electric Fields May Guide Neocortlcai Network Activity, Neuron, Jul. 15, 2010, Voi. 67, pp. 129-143.
Frye, R.E. et al., Transcrania! Magnetic Stimulation in Child Neurology: Current and Future Directions, Journal of Child Neurology, Jan. 2008, vol. 23, No. 1, pp. 79-96.
George, M.S. et al,, the Expanding Evidence Base for rTMS Treatment of Depression, Current Opinion on Psychiatry, Jan. 2013, vol. 26, No. 1, pp. 13-18.
Gonzalez-Rosa, J.J. et al . . . , Static Magnetic Field Stimulation over the Visual Cortex increases Alpha Oscillations and Slows Visual Search in Humans, The Journal of Neuroscience, Jun. 17, 2015, Voi. 35, No. 24, pp. 9182-9193.
Guse, B. et al., Cognitive effects of high-frequency repetitive transcranial magnetic stimulation: a systematic review, Journal of Neural Transmission, 2010, 117: 105-22.
Helekar Santosh A., In Defense of Experience—Coding Nonarbitrary Temporal Neural Activity Patterns, Consciousness and Cognition, Dec. 1999, pp. 455-461, vol. 8, issue 4.
Helekar, S.A. et al., Electromyographic motor-evoked potentials elicited by transcranial magnetic stimulation with rapidly moving permanent magnets mounted on a multisite stimulator cap, Presentation Abstract, Nov. 13, 2013.
Helekar, Santosh A., On the Possibility of Universal Neural Coding of Subjective Experience, Consciousness and Cognition, Dec. 1999, pp. 423-446, vol. 8, Issue 4.
Helekar, Santosh et al., Transcranial Brain Simulation With Rapidly Spinning High-Field Permanent Magnets, IEEE Access, vol. 4, May 19, 2016, pp. 2520-2527.
Helfrich, R.F. et al., Entrainment of Brain Oscillations by Transcranial Alternating Current Stimulation, Current Biology, Feb. 3, 20147, vol. 24, pp. 333-339.
Huerta, P. T. et al., Transcranial magnetic stimulation, synaptic plasticity and network oscillations, Journal of NeuroEngineering and Rehabilitation, 2009, 6:7.
Ilic, T. V. et al., Exploring Motor Cortical Plasticity Using Transcranial Magnetic Stimulation in Humans, Annals of the New York Academy of Sciences, 2005, vol. 1048(1): 175-184.
International Preliminary Report on Patentability for Application No. PCT/US2014/027900, dated Sep. 15, 2015.
International Preliminary Report on Patentability for Application No. PCT/US2014/051340, dated Feb. 16, 2016.
International Search Report and Written Opinion for Application No. PCT/US2014/027900, dated Sep. 4, 2014.
International Search Report and Written Opinion for Application No. PCT/US2014/051340, dated Apr. 15, 2015.
International Search Report and Written Opinion for Application No. PCT/US2017/031413, dated Aug. 14, 2017.
Jin, Y. et al., A Pilot Study of the Use of EEG-Based SynchornIzed Transcranial Magnetic Stimulation (sTMS) for Treatment of Major Depression, BMC Psychiatry, 2014, Voi. 14, No. 13, pp. 1-6.
Kamitani, Y. et al., Manifestation of scotomas created by transcranial magnetic stimulation of human visual cortex, Nature Neuroscience, 1999, 2(8): 767-71.
Kamke, M. R. et al., Parietal disruption alters audiovisual binding in the sound-induced flash illusion, NeuroImage 62, 2012, 1334-1341.
Kammer, T., Masking visual stimuli by transcranial magnetic stimulation, Psychological Research, 2007, 71: 659-66.
Leuchter, A. F. et al., Synchronized Transcranial Magnetic Stimulation (sTMS) Efficacy and Safety of Low-field Synchronized Transcranial Magnetic Stimulation (sTMS) for Treatment of Major Depression, Brain Stimulation, 2015, 1-8.
Levasseur-Moreau, J. et al., Translational application of neuromodulation of decision-making, Brain Stimulation 5, 2012, 77-83.
Lipton, R. B. et al., Transcranial Magnetic Simulation in the Treatment of Migraine, Neurotherapeutics: The Journal of the American Society for Experimental NeuroTherapeutics, 2010, vol. 7, 204-12.
Muller, P. A. et al., Safety and tolerability of repetitive transcranial magnetic stimulation in patients with pathologic positive sensory phenomena: a review of literature, Brain Stimulation, 2012, 5(3): 320-329.
Muller-Dahlhaus, F. et al., Plasticity resembling spike-timing dependent synaptic plasticity: the evidence in human cortex, Frontiers in Synaptic Neuroscience, 2010, vol. 2, Article 34, 1-11.
Nakatani-Enomoto, S. et al., Bidirectional modulation of sensory cortical excitability by quadripulse transcranial magnetic stimulation (QPS) in humans, Clinical Neurophysiology 123, 2012, 1415-1421.
Olivierg, A. et al., Transcranial Static Magnetic Field Stimulation of the Human Motor Cortex, Journal of Physiology, 2011, vol. 589, No. 20, pp. 4949-4958.
Pitcher, D. et al., Transcranial Magnetic Stimulation Disrupts the Perception and Embodiment of Facial Expressions, The Journal of Neuroscience, 2008, 28(36): 8929-33.
Rivadulla, C. et al., Magnetic Field Strength and Reproducibility of Neodymium Magnets Usefui for Transcranial Static Magnetic Field Stimulation of the Human Cortex, Neuromodulation: Technology at the Neural interface, 2014, vol. 17, No. 5, pp. 438-442.
Rossi S. et al., Safety, ethical considerations, and application guidelines for the use of transcranial magnetic stimulation in clinical practice and research, Clinical Neurophysiology, 2009, 2008-2039.
Sanchez, Alvaro et al., Antimagnets: Controlling Magnetic Fields With Superconductor—Metamaterial Hybrids, New Journal of Physics, 2011, vol. 13.
Sandrini, M. et al., The use of transcranial magnetic stimulation in cognitive neuroscience: A new synthesis of methodological issues, Neuroscience and Biobehavioral Reviews 35, 2011, 516-536.
Second Office Action for Chinese Application No. 201480027788.3, dated Aug. 14, 2017.
Thielscher, A, et al., Linking Physics with Physiology in TMS: A Sphere Field Model to Determine the Cortical Stimulation Site in TMS, Neuroimage, 2002, vol. 17, pp. 1117-1130.
Third Office Action for Chinese Application No. 201480027788.3, dated Mar. 6, 2018.
Wassermann, E. M. et al., Transcranial Magnetic Brain Stimulation: Therapeutic Promises and Scientific Gaps, Pharmacology and Therapeutics, 2012, 133(1): 98-107.
Wassermann, E. M., Risk and safety of repetitive transcranial magnetic stimulation: report and suggested guidelines from the International Workshop on the Safety of Repetitive Transcranial Magnetic Stimulation, Jun. 5-7, 1996, Electroencephalographyand Clinical Neurophysiology, 1998, 108, 1-16.
Zaehle, T. et al., Transcranial Alternating Current Stimulation Enhances Individual Alpha Activity in Human EEG, PloS one, Nov. 2010, vol. 5, No. 11, pp. 1-7.
Third Office Action for Chinese Application No. 201480057016.4, dated Sep. 12, 2019.
Office Action for Canadian Application No. 2,942,653, dated Jul. 19, 2019.
Second Office Action for Chinese Application No. 201480057016.4, dated Apr. 3, 2019.

(56) References Cited

OTHER PUBLICATIONS

Office Action, European Patent Application No. 14771163.4, dated Mar. 20, 2019.
International Preliminary Report on Patentability for Application No. PCT/US2017/031413, dated Nov. 15, 2018.
First Examination Report for IN Application No. 201617008498, dated May 19, 2020.
Examination Report for BR Application No. 112015022834-8, dated Jul. 5, 2020.
First Examination Report for IN Application No. 9216/DELNP/2015, dated Jun. 5, 2020.
Examination Report for BR Application No. 112016003147-4, dated Aug. 11, 2020.

COMPARISON OF PRESENT INVENTION WITH CONVENTIONAL TMS

|  | Present Invention | Conventional TMS |
|---|---|---|
| Type of Magnet | Permanent Neodymium | Electromagnetic Coil |
| Maximum Field Strength | 1.48 T | 2.2 T |
| dB/dt | 500 - 5000 T/s | 5000 - 20,000 T/s |
| Stimulus Duration | 1 - 500 ms | 0.3 - 5 ms |
| Repetition Rate | 0.1 - 10 Hz | 0.1 - 50 Hz |
| Stimulation Sites | Multiple (1 - 32) | Single |
| Dynamic Modulation | Present | Absent |
| User Interaction | Present | Absent |
| Current for Stimulation | None | 4000 A |
| Power Supply | DC Battery (9 - 12 V) | AC Main (110 - 220 V) |
| Risk of Electric Shock | Absent | Present |
| Risk of Burns | Absent | Present |
| Risk of Seizure | Absent | Present at high rates |

FIG. 6

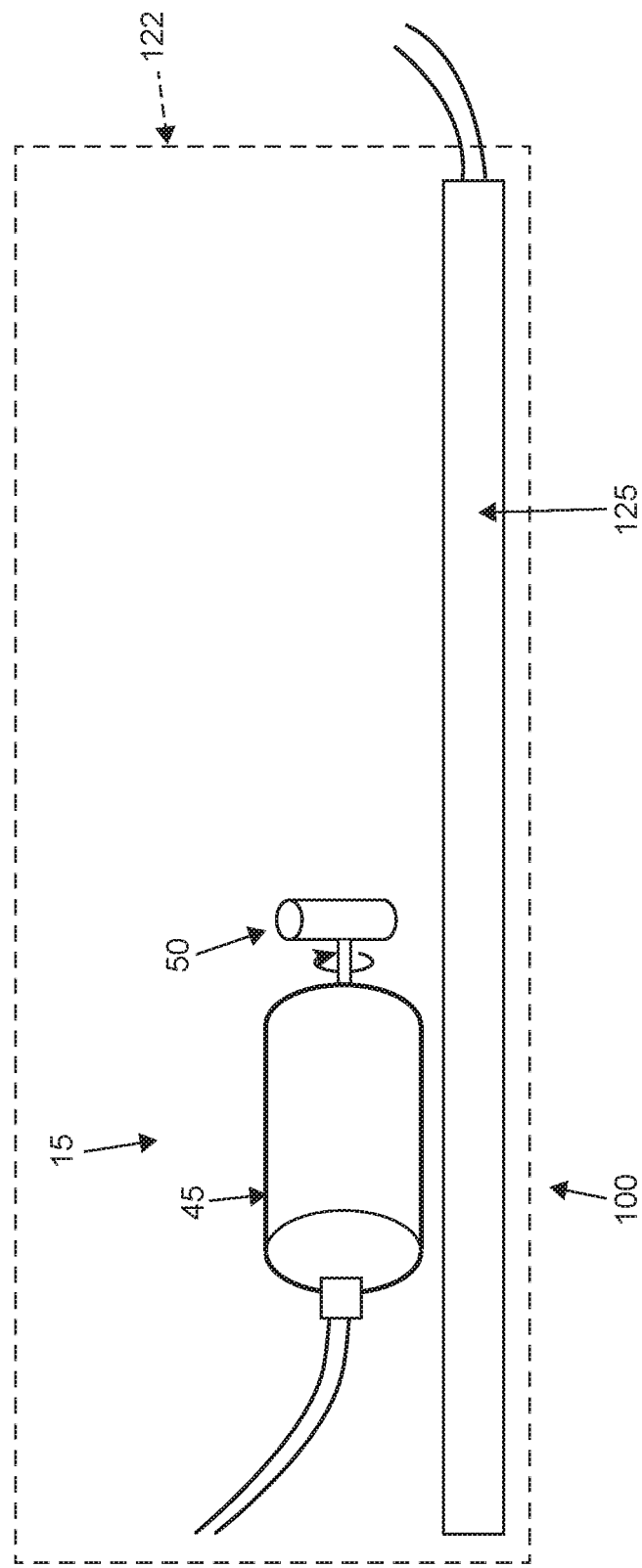

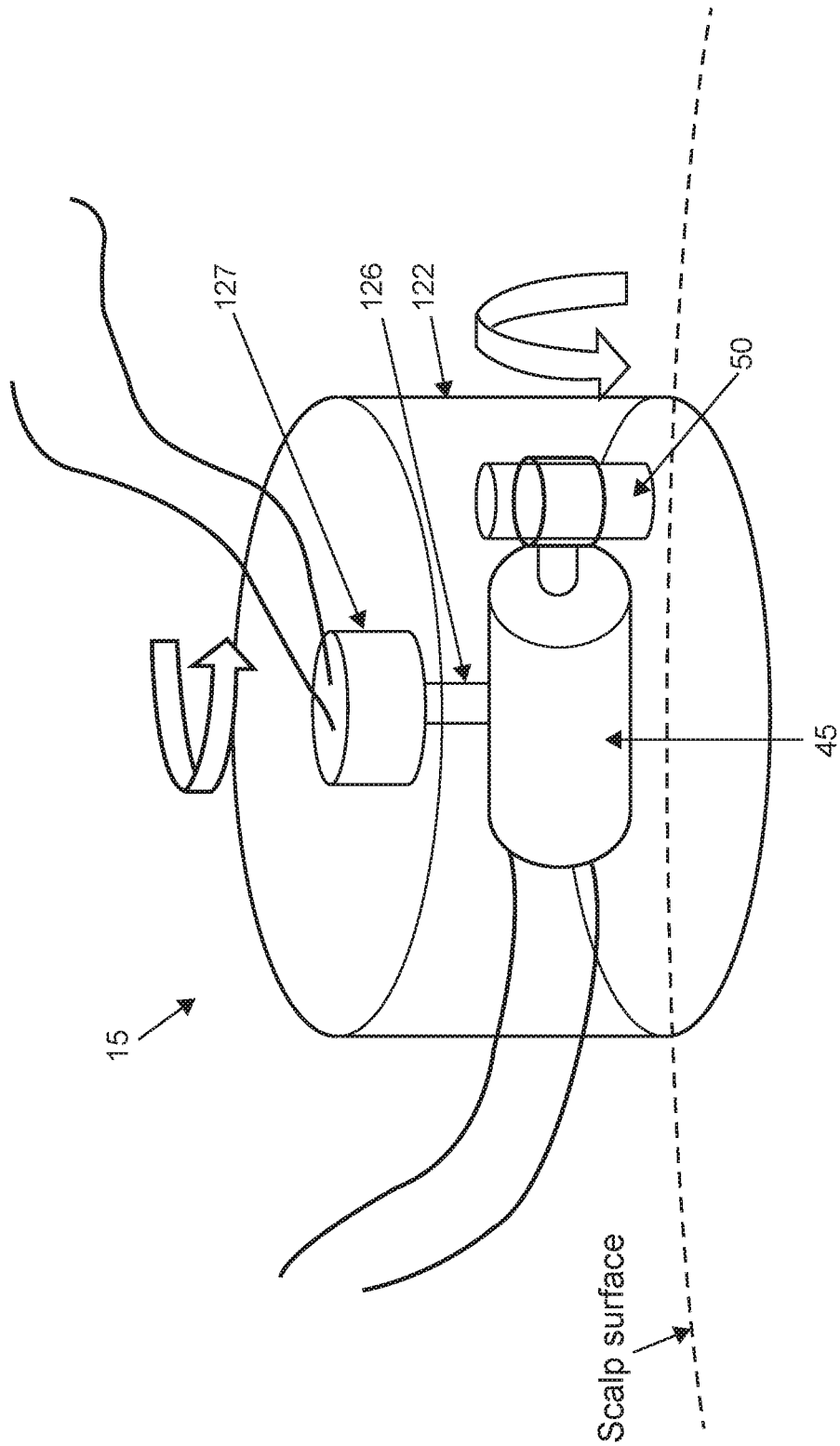

METHOD AND APPARATUS FOR PROVIDING TRANSCRANIAL MAGNETIC STIMULATION (TMS) TO AN INDIVIDUAL

REFERENCE TO PENDING PRIOR PATENT APPLICATIONS

This patent application:

(1) is a continuation-in-part of prior U.S. patent application Ser. No. 14/912,004, filed Feb. 12, 2016 by The Methodist Hospital et al. and Santosh A. Helekar et al. for METHOD AND APPARATUS FOR PROVIDING TRANSCRANIAL MAGNETIC STIMULATION (TMS) TO AN INDIVIDUAL, which patent application:

(A) claims benefit of prior International (PCT) Patent Application No. PCT/US2014/051340, filed Aug. 15, 2014 by The Methodist Hospital for METHOD AND APPARATUS FOR PROVIDING TRANSCRANIAL MAGNETIC STIMULATION (TMS) TO AN INDIVIDUAL, which patent application in turn:

(i) claims benefit of prior International (PCT) Patent Application No. PCT/US14/27900, filed Mar. 14, 2014 by The Methodist Hospital for METHOD AND APPARATUS FOR PROVIDING TRANSCRANIAL MAGNETIC STIMULATION (TMS) TO A PATIENT, which claims benefit of prior U.S. patent application Ser. No. 13/829,349, filed Mar. 14, 2013 by The Methodist Hospital Research Institute and Santosh A. Helekar et al. for METHOD AND APPARATUS FOR PROVIDING TRANSCRANIAL MAGNETIC STIMULATION (TMS) TO A PATIENT; and (ii) claims benefit of prior U.S. Provisional Patent Application Ser. No. 61/866,447, filed Aug. 15, 2013 by The Methodist Hospital Research Institute and Santosh A. Helekar et al. for METHOD AND APPARATUS FOR PROVIDING TRANSCRANIAL MAGNETIC STIMULATION (TMS) TO A PATIENT;

(B) is a continuation-in-part of prior U.S. patent application Ser. No. 13/829,349, filed Mar. 14, 2013 by The Methodist Hospital Research Institute and Santosh A. Helekar et al. for METHOD AND APPARATUS FOR PROVIDING TRANSCRANIAL MAGNETIC STIMULATION (TMS) TO A PATIENT;

(C) is a continuation-in-part of prior International (PCT) Patent Application No. PCT/US14/27900, filed Mar. 14, 2014 by The Methodist Hospital and Santosh A. Helekar et al. for METHOD AND APPARATUS FOR PROVIDING TRANSCRANIAL MAGNETIC STIMULATION (TMS) TO A PATIENT, which claims benefit of prior U.S. patent application Ser. No. 13/829,349, filed Mar. 14, 2013 by The Methodist Hospital Research Institute and Santosh A. Helekar et al. for METHOD AND APPARATUS FOR PROVIDING TRANSCRANIAL MAGNETIC STIMULATION (TMS) TO A PATIENT; and (D) claims benefit of prior U.S. Provisional Patent Application Ser. No. 61/866,447, filed Aug. 15, 2013 by The Methodist Hospital Research Institute and Santosh A. Helekar et al. for METHOD AND APPARATUS FOR PROVIDING TRANSCRANIAL MAGNETIC STIMULATION (TMS) TO A PATIENT; and (2) claims benefit of prior U.S. Provisional Patent Application Ser. No. 62/332,087, filed May 5, 2016 by The Methodist Hospital et al. and Santosh A. Helekar et al. for TRANSCRANIAL BRAIN STIMULATION WITH RAPIDLY SPINNING HIGH-FIELD PERMANENT MAGNETS.

The six (6) above-identified patent applications are hereby incorporated herein by reference.

FIELD OF THE INVENTION

This invention relates to Transcranial Magnetic Stimulation (TMS) in general, and more particularly to novel methods and apparatus for providing transcranial magnetic stimulation to an individual.

BACKGROUND OF THE INVENTION

Transcranial Magnetic Stimulation (TMS) is a non-invasive procedure in which magnetic stimulation is applied to the brain in order to modify the natural electrical activity of the brain, whereby to provide therapy to an individual, to assist in diagnosis and/or to map out brain function in neuroscience research. More particularly, TMS applies a rapidly changing magnetic field to the brain of an individual in order to induce weak electric currents in the brain of the individual through electromagnetic induction. These weak electric currents modify the natural electrical activity of the brain of the individual, whereby to provide therapy to the individual, to assist in diagnosis and/or to map out brain function in neuroscience research. TMS has been approved by the Food and Drug Administration (FDA) for treating depression. TMS is also currently being investigated in the management of various other neurological and psychiatric disorders, including stroke, migraines, Parkinson's disease, tinnitus, autism, schizophrenia, etc. TMS is also being used to study brain function in neuroscience research.

Conventional TMS apparatus generally comprises an electromagnetic coil which is fixed in position relative to the head of the individual. Since the magnetic field applied to the individual is a function of the configuration of the electromagnetic coil, the current passed through the electromagnetic coil, and the location of the electromagnetic coil relative to the individual, the fixed construction of conventional TMS apparatus significantly limits the character of the magnetic field which can be applied to the individual, and hence significantly limits the TMS therapy which can be provided to the individual. In addition, conventional TMS apparatus generally utilizes very high electric currents in the electromagnetic coil, which raises the risk of accidental injury to the individual through electric shocks, burns, seizures, etc.

The present invention addresses the foregoing problems associated with the prior art by providing an improved method and apparatus for providing Transcranial Magnetic Stimulation (TMS) to an individual. In addition, the present invention also provides additional advantages over conventional TMS, e.g., (i) it comprises a portable, wearable device that can be used outside of a medical or research facility, e.g., at home; (ii) individuals can self-administer a prescribed treatment regimen at home through handheld, or worn, wired or wireless electronic controllers; (iii) it comprises multiple magnetic stimulators directable at multiple brain structures which can lead to better treatment, diagnostic testing and/or insight into brain function through its use in neuroscience research; (iv) it comprises multiple magnetic stimulators directable at a particular brain structure which can be more effective because they can induce current flow in multiple orientations; and (v) it comprises multiple magnetic stimulators which can aggregate their magnetic fields for more robust brain stimulation.

SUMMARY OF THE INVENTION

The present invention provides a novel method and apparatus for providing Transcranial Magnetic Stimulation (TMS) to an individual. Among other things, the present invention comprises the provision and use of novel TMS apparatus which allows the spatial, strength and temporal characteristics of the magnetic field generated by the TMS apparatus to be custom tailored for each individual, whereby to provide individual-specific TMS therapy and/or diagnostic testing. It also affords greater flexibility in open-ended investigations of brain function in neuroscience research.

In one form of the invention, there is provided apparatus for applying Transcranial Magnetic Stimulation (TMS) to an individual, wherein the apparatus comprises:

a head mount for disposition on the head of an individual; and a plurality of magnet assemblies for releasable mounting on the head mount, wherein each of the magnet assemblies comprises a permanent magnet, and at least one of (i) a movement mechanism for moving the permanent magnet and/or (ii) a magnetic shield shutter mechanism, for selectively providing a rapidly changing magnetic field capable of inducing weak electric currents in the brain of an individual so as to modify the natural electrical activity of the brain of the individual;

wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each individual, whereby to provide individual-specific TMS therapy and/or diagnostic testing, as well as greater flexibility in open-ended investigations of brain function in neuroscience research.

In one preferred form of the invention, each of the magnet assemblies is configured to provide a rapidly changing magnetic field of at least 500-600 Tesla/second.

In another form of the invention, there is provided a method for providing Transcranial Magnetic Stimulation (TMS) to an individual, the method comprising:

providing apparatus comprising:

a head mount for disposition on the head of an individual; and a plurality of magnet assemblies for releasable mounting on the head mount, wherein each of the magnet assemblies comprises a permanent magnet, and at least one of (i) a movement mechanism for moving the permanent magnet and/or (ii) a magnetic shield shutter mechanism, for selectively providing a rapidly changing magnetic field capable of inducing weak electric currents in the brain of an individual so as to modify the natural electrical activity of the brain of the individual;

positioning the head mount on the head of the individual, and positioning a selected number of magnet assemblies on the head mount at selected locations; and selectively providing a rapidly changing magnetic field with at least one of the magnet assemblies;

wherein the number of magnet assemblies mounted on the head mount, their individual positioning on the head mount, and their selective provision of a rapidly changing magnetic field is selected so as to custom tailor the spatial, strength and temporal characteristics of the magnetic field for that individual, whereby to provide individual-specific TMS therapy and/or diagnostic testing, as well as greater flexibility in open-ended investigations of brain function in neuroscience research.

In one preferred form of the invention, each of the magnet assemblies is configured to provide a rapidly changing magnetic field of at least 500-600 Tesla/second.

In another form of the invention, there is provided apparatus for applying Transcranial Magnetic Stimulation (TMS) to an individual, wherein the apparatus comprises:

a head mount for disposition on the head of an individual; and a plurality of magnet assemblies mounted on the head mount in a predetermined pattern, wherein each of the magnet assemblies comprises a permanent magnet, and at least one of (i) a movement mechanism for moving the permanent magnet and/or (ii) a magnetic shield shutter mechanism, for selectively providing a rapidly changing magnetic field capable of inducing weak electric currents in the brain of an individual so as to modify the natural electrical activity of the brain of the individual;

wherein the number of magnet assemblies mounted on the head mount, their individual positioning on the head mount, and their selective provision of a rapidly changing magnetic field is selected so as to allow the spatial, strength and temporal characteristics of the magnetic field to be custom tailored for each individual, whereby to provide individual-specific TMS therapy, to assist in diagnosis and/or to map out brain function in neuroscience research.

In one preferred form of the invention, each of the magnet assemblies is configured to provide a rapidly changing magnetic field of at least 500-600 Tesla/second.

In another form of the invention, there is provided a method for providing Transcranial Magnetic Stimulation (TMS) to an individual, the method comprising:

providing apparatus comprising:

a head mount for disposition on the head of an individual; and a plurality of magnet assemblies mounted on the head mount in a predetermined pattern, wherein each of the magnet assemblies comprises a permanent magnet, and at least one of (i) a movement mechanism for moving the permanent magnet and/or (ii) a magnetic shield shutter mechanism, for selectively providing a rapidly changing magnetic field capable of inducing weak electric currents in the brain of an individual so as to modify the natural electrical activity of the brain of the individual;

positioning the head mount on the head of the individual; and selectively providing a rapidly changing magnetic field with at least one of the magnet assemblies;

wherein the number of magnet assemblies mounted on the head mount, their individual positioning on the head mount, and their selective provision of a rapidly changing magnetic field is selected so as to custom tailor the spatial, strength and temporal characteristics of the magnetic field for that individual, whereby to provide individual-specific TMS therapy, to assist in diagnosis and/or to map out brain function in neuroscience research.

In one preferred form of the invention, each of the magnet assemblies is configured to provide a rapidly changing magnetic field of at least 500-600 Tesla/second.

In another form of the invention, there is provided apparatus for creating a variable magnetic field in a region of space, the apparatus comprising:

at least one mount for disposition near the region of space; and a plurality of magnet assemblies for mounting on the at least one mount, wherein each of the magnet assemblies comprises a permanent magnet, and at least one of (i) a movement mechanism for moving the permanent magnet and/or (ii) a magnetic shield shutter mechanism, for selectively providing a variable magnetic field in the region of space;

wherein the number of magnet assemblies mounted on the at least one mount, their individual positioning on the at least one mount, and the characteristics of their individual variable magnetic fields are selected so as to tailor the spatial, strength and temporal characteristics of the variable magnetic field created in the region of space.

In another form of the invention, there is provided a method for creating a variable magnetic field in a region of space, the method comprising:

providing apparatus comprising:

at least one mount for disposition near the region of space; and a plurality of magnet assemblies for mounting on the at least one mount, wherein each of the magnet assemblies comprises a permanent magnet, and at least one of (i) a movement mechanism for moving the permanent magnet and/or (ii) a magnetic shield shutter mechanism, for selectively providing a variable magnetic field in the region of space;

positioning the at least one mount near the region of space, and positioning a selected number of magnet assemblies on the at least one mount at selected locations; and for at least one of the magnet assemblies positioned on the at least one mount, selectively moving at least one of the permanent magnet and/or the magnetic shield shutter mechanism so as to provide a variable magnetic field in the region of space;

wherein the number of magnet assemblies mounted on the at least one mount, their individual positioning on the at least one mount, and the characteristics of their individual variable magnetic fields are selected so as to tailor the spatial, strength and temporal characteristics of the variable magnetic field created in the region of space.

In another form of the invention, there is provided apparatus for creating a variable magnetic field in a region of space, the apparatus comprising:

a permanent magnet for disposition near the region of space; and at least one of (i) a movement mechanism for moving the permanent magnet so as to create a variable magnetic field in the region of space and/or (ii) a magnetic field shutter mechanism for creating a variable magnetic field in the region of space.

In another form of the invention, there is provided a method for creating a variable magnetic field in a region of space, the method comprising:

providing apparatus comprising:

at least one of (i) a movement mechanism for moving the permanent magnet so as to create a variable magnetic field in the region of space and/or (ii) a magnetic field shutter mechanism for creating a variable magnetic field in the region of space;

positioning the permanent magnet near the region of space; and selectively moving at least one of the permanent magnet and/or the magnetic shield shutter mechanism so as to provide a variable magnetic field in the region of space.

In another form of the invention, there is provided apparatus for applying Transcranial Magnetic Stimulation (TMS) to the brain of an individual, wherein the apparatus comprises:

a head mount for disposition on the head of an individual;

a plurality of magnet assemblies for releasable mounting on the head mount, wherein each of the magnet assemblies comprises a permanent magnet, and at least one of (i) a movement mechanism for moving the permanent magnet and/or (ii) a magnetic shield shutter mechanism, whereby to provide a rapidly changing magnetic field; and a computerized controller for operating at least one of the movement mechanism and the magnetic shield shutter mechanism of at least one of the magnet assemblies so as to apply a rapidly changing magnetic field to the brain of the individual, wherein the computerized controller is configured to operate at least one of the movement mechanism and the magnetic shield shutter mechanism of the at least one of the magnet assemblies so that the at least one magnet assembly provides one from the group consisting of intermittent oscillatory stimulation and continuous oscillatory stimulation, whereby to induce weak electric currents in the brain of an individual so as to modify the natural electrical activity of the brain of the individual.

In another form of the invention, there is provided a method for providing Transcranial Magnetic Stimulation (TMS) to an individual, the method comprising:

providing apparatus comprising:

a head mount for disposition on the head of an individual;

a plurality of magnet assemblies for releasable mounting on the head mount, wherein each of the magnet assemblies comprises a permanent magnet, and at least one of (i) a movement mechanism for moving the permanent magnet and/or (ii) a magnetic shield shutter mechanism, whereby to provide a rapidly changing magnetic field; and a computerized controller for operating at least one of the movement mechanism and the magnetic shield shutter mechanism of at least one of the magnet assemblies so as to apply a rapidly changing magnetic field to the brain of the individual, wherein the computerized controller is configured to operate at least one of the movement mechanism and the magnetic shield shutter mechanism of the at least one of the magnet assemblies so that the at least one magnet assembly provides one from the group consisting of intermittent oscillatory stimulation and continuous oscillatory stimulation, whereby to induce weak electric currents in the brain of an individual so as to modify the natural electrical activity of the brain of the individual;

positioning the head mount on the head of the individual, and positioning a selected number of magnet assemblies on the head mount at selected locations; and selectively providing a rapidly changing magnetic field with at least one of the magnet assemblies.

In another form of the invention, there is provided apparatus for applying Transcranial Magnetic Stimulation (TMS) to an individual, wherein the apparatus comprises:

a head mount for disposition on the head of an individual;

a plurality of magnet assemblies mounted on the head mount in a predetermined pattern, wherein each of the magnet assemblies comprises a permanent magnet, and at least one of (i) a movement mechanism for moving the permanent magnet and/or (ii) a magnetic shield shutter mechanism, whereby to provide a rapidly changing magnetic field; and a computerized controller for operating at least one of the movement mechanism and the magnetic shield shutter mechanism of at least one of the magnet assemblies so as to apply a rapidly changing magnetic field to the brain of the individual, wherein the computerized controller is configured to operate at least one of the movement mechanism and the magnetic shield shutter mechanism of the at least one of the magnet assemblies so that the at least one magnet assembly provides one from the group consisting of intermittent oscillatory stimulation and continuous oscillatory stimulation, whereby to induce weak electric currents in the brain of an individual so as to modify the natural electrical activity of the brain of the individual.

In another form of the invention, there is provided a method for providing Transcranial Magnetic Stimulation (TMS) to an individual, the method comprising:

providing apparatus comprising:

a head mount for disposition on the head of an individual;

a plurality of magnet assemblies mounted on the head mount in a predetermined pattern, wherein each of the magnet assemblies comprises a permanent magnet, and at least one of (i) a movement mechanism for moving the permanent magnet and/or (ii) a magnetic shield shutter mechanism, whereby to provide a rapidly changing magnetic field; and a computerized controller for operating at least one of the movement mechanism and the magnetic shield shutter mechanism of at least one of the magnet assemblies so as to apply a rapidly changing magnetic field to the brain of the individual, wherein the computerized controller is configured to operate at least one of the movement mechanism and the magnetic shield shutter mechanism of the at least one of the magnet assemblies so that the at least one magnet assembly provides one from the group consisting of intermittent oscillatory stimulation and continuous oscillatory stimulation, whereby to induce weak electric currents in the brain of an individual so as to modify the natural electrical activity of the brain of the individual;

positioning the head mount on the head of the individual; and selectively providing a rapidly changing magnetic field with at least one of the magnet assemblies.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIG. 6 is a table illustrating some of the advantages of the present invention over conventional TMS;

FIG. 12 is a schematic view illustrating still another form of magnet shield shutter mechanism; and FIG. 13 is a schematic view illustrating novel apparatus for providing TMS to an individual, wherein the magnet assemblies further comprise a servomotor for changing the orientation of the rotating permanent magnet.

DETAILED DESCRIPTION OF THE PREFERRED EMBODIMENTS

Head-Mounted Transcranial Magnetic Stimulation (TMS) Apparatus

Figure 1:
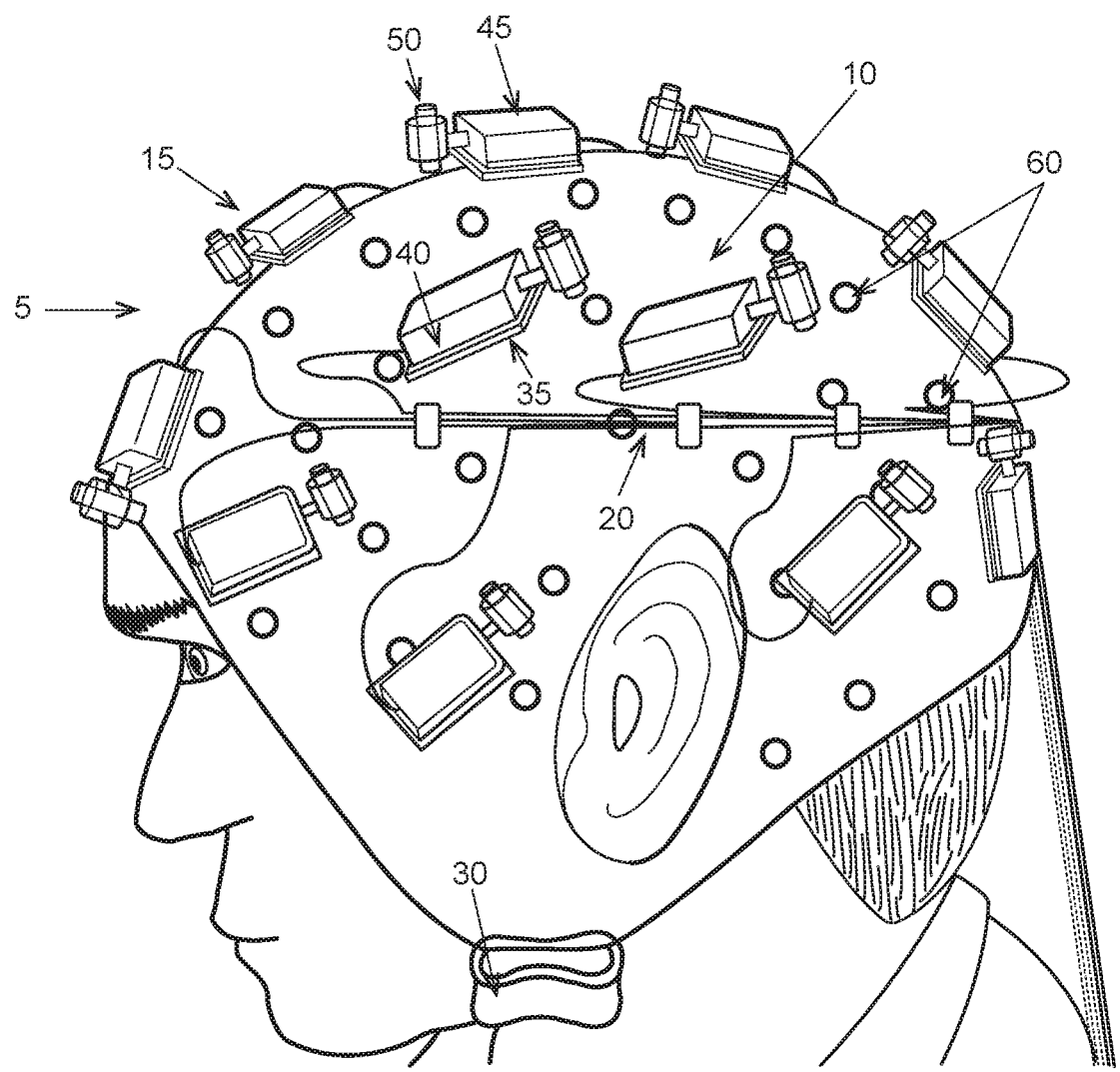
FIGS. 1 and 2 are schematic views illustrating novel apparatus for providing Transcranial Magnetic Stimulation (TMS) to an individual.
Figure 2:
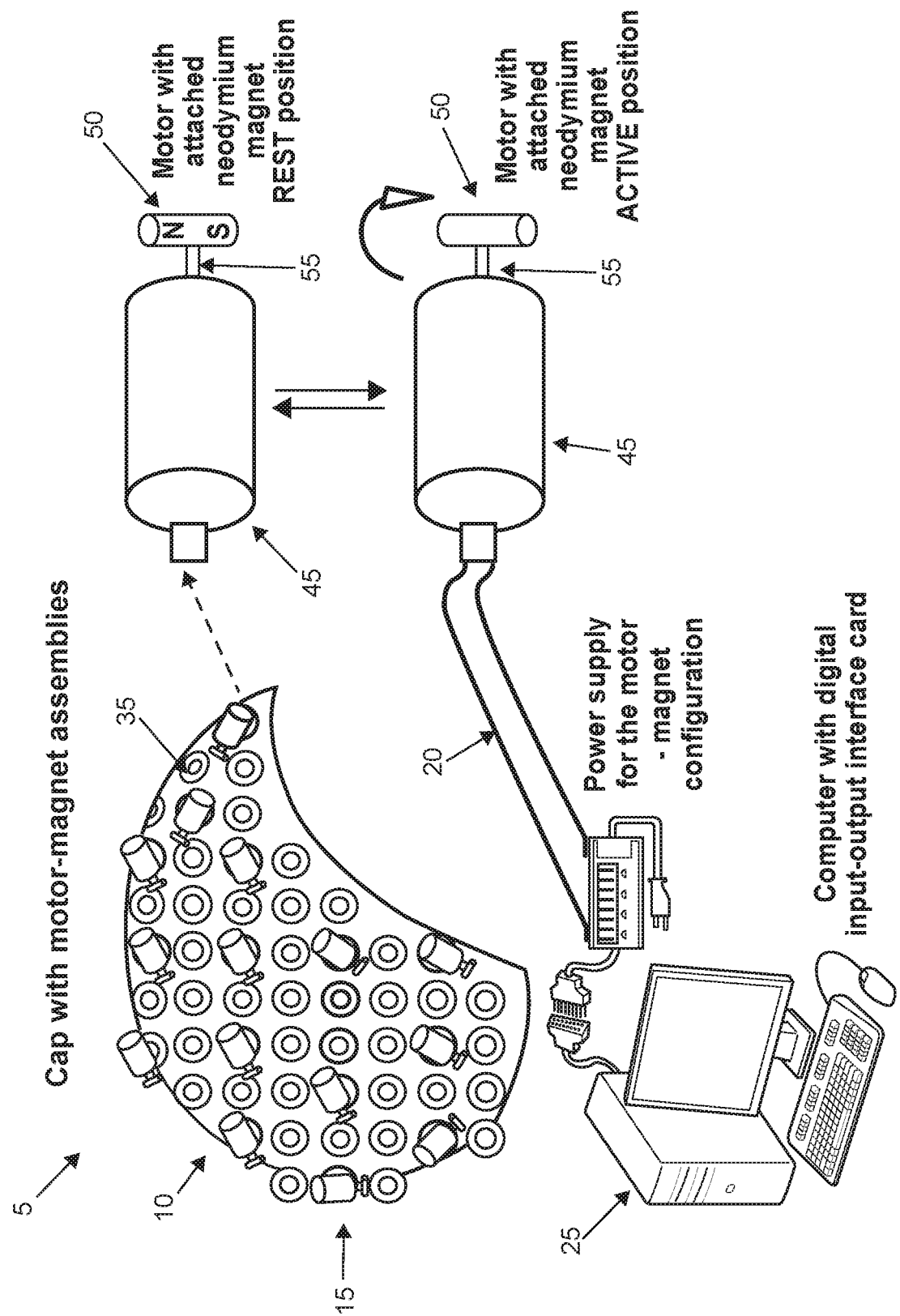

Looking first at FIGS. 1 and 2, there is shown novel Transcranial Magnetic Stimulation (TMS) apparatus 5 for providing TMS to an individual. Among other things, and as will hereinafter be discussed, novel TMS apparatus 5 allows the spatial, strength and temporal characteristics of the magnetic field generated by the TMS apparatus to be custom tailored for each individual, whereby to provide individual-specific TMS therapy, to assist in diagnosis and/or to map out brain function in neuroscience research.

More particularly, TMS apparatus 5 generally comprises a head mount 10 for positioning on the head of an individual, a plurality of magnet assemblies 15 which are releasably mounted to head mount 10, and a plurality of leads 20 for connecting each of the magnet assemblies 15 to a computerized controller 25. Computerized controller 25 may be a self-standing device or, if desired, computerized controller 25 may be wearable, e.g., on a waistband, an armband, etc. Additionally, if desired, magnet assemblies 15 may be connected to computerized controller 25 wirelessly, whereby to eliminate the need for leads 20.

In one preferred form of the invention, head mount 10 comprises a soft, form-fitting skull cap adapted to cover the head of the individual while leaving the face and ears of the individual exposed. Head mount 10 is intended to provide a stable support for the aforementioned magnet assemblies 15, and to that end head mount 10 preferably comprises a textile construct (e.g., woven, braided or knit fibers) that has a stable structure but which can breathe (for comfort of the individual). Alternatively, the head mount could be constructed of other materials such as soft plastic. Head mount 10 preferably includes a chin strap 30 so that the head mount can be fastened onto the head of an individual with light tension, whereby to ensure that the head mount maintains a fixed position on the head of the individual.

As noted above, a plurality of magnet assemblies 15 are releasably mounted to head mount 10. More particularly, magnet assemblies 15 are releasably mounted to head mount 10 so that the number of magnet assemblies 15, and/or their individual positioning on head mount 10, can be varied as desired by the clinician or investigator. To this end, head mount 10 preferably comprises a plurality of fastener bases 35 which are distributed about the outer surface of head mount 10, and each of the magnet assemblies 15 preferably comprises a counterpart fastener connect 40 adapted to mate with a fastener base 35, whereby to allow each magnet assembly 15 to be releasably secured to head mount 10 substantially anywhere about the surface of the head mount. It will be appreciated that, as a result of this construction, it is possible to releasably secure the desired number of magnet assemblies 15 to head mount 10, at the desired locations for those magnet assemblies 15, so that the number of magnet assemblies 15, and/or their positioning on head mount 10, can be varied as desired by the clinician or investigator.

By way of example but not limitation, head mount 10 may comprise a woven fabric skull cap covering the skull of the individual, the plurality of fastener bases 35 disposed on head mount 10 may each comprise one half of a conventional hook-and-loop (e.g., Velcro™) fastener, and the fastener connects 40 of the magnet assemblies 15 may each comprise the second half of a conventional hook-and-loop (e.g., Velcro™) fastener. In this way, each of the magnet assemblies 15 may be releasably fastened to a fastener base 35, and hence to head mount 10. Alternatively, means other than conventional hook-and-loop (e.g., Velcro™) fasteners (e.g., mechanical fasteners, snap fasteners, etc.) may be used to releasably secure magnet assemblies 15 to head mount 10.

In one preferred form of the invention, magnet assemblies 15 each comprise a motor 45 and a permanent magnet 50. Permanent magnet 50 is mounted to the drive shaft 55 of motor 45, such that when motor 45 is energized, permanent magnet 50 will rotate, whereby to provide a rapidly changing magnetic field about the magnet assembly. In one preferred form of the invention, each of the magnet assemblies 15 comprises a permanent magnet 50 for selectively providing a rapidly changing magnetic field of at least 500-600 Tesla/second corresponding to a magnet movement speed of no less than 400 Hertz. As will be appreciated by those knowledgeable in the field of TMS, by applying this rapidly changing magnetic field of at least 500-600 Tesla/second, corresponding to magnet movement speed of no less than 400 Hertz, to the brain of an individual, weak electric currents can be induced in the neurons of the brain of the individual. These weak electric currents modify the natural electrical activity of the brain of the individual, whereby to provide therapy to the individual, to assist in diagnosis and/or to map out brain function in neuroscience research. In one preferred form of the invention, motor 45 is a variable speed motor, such that permanent magnet 50 may be rotated faster or slower, as desired, whereby to adjust the voltage of the electric currents induced in the neurons of the brain of the individual, as will hereinafter be discussed in further detail. In one preferred form of the invention, permanent magnet 50 comprises a rare earth magnet, e.g., a neodymium magnet.

TMS apparatus 5 also comprises a computerized controller 25 for independently controlling the operation of each of the magnet assemblies 15, i.e., turning motors 45 on or off, regulating the speeds of motor rotation, etc. Leads 20 connect computerized controller 25 to each of the magnet assemblies 15.

Computerized controller 25 may be configured to provide two different modes of TMS stimulation using magnet assemblies 15. These two different modes can be characterized as: (i) intermittent oscillatory stimulation, and (ii) continuous oscillatory stimulation.

With intermittent oscillatory stimulation, short bursts (or "packets") of "wavy" TMS stimuli ("stimulus waves") are delivered at periodic intervals. In one preferred form of the invention, the stimulus waves or oscillations within each burst or packet have a frequency of approximately 400 Hz, although they may have a frequency higher or lower than 400 Hz. In one preferred form of the invention, the burst (packet) durations range from approximately 1-500 ms. In one preferred form of the invention, the silent intervals between bursts (packets) range from about 100-10,000 ms, corresponding to stimulation rates of about 10-0.1 Hz. Computerized controller 25 is configured so that the durations and rates of stimulation within a stimulation session can be dynamically varied.

With continuous oscillatory stimulation, the "wavy" stimuli are delivered throughout the duration of a stimulation session that can last from a few seconds to several minutes. In one preferred form of the invention, the frequency of the stimulus waves of the continuous oscillatory stimulation is approximately 400 Hz, although they may have a frequency higher or lower than 400 Hz. The frequency of the stimulus waves can be dynamically varied at fixed periodic or variable intervals using pulse width modulation with resultant variation in stimulus strength.

Both methods of stimulation (i.e., intermittent oscillatory stimulation and continuous oscillatory stimulation) can be implemented separately or simultaneously in multiple magnet assemblies 15 activated at the same time. Both sets of stimulus parameters can also be varied independently, for each of several simultaneously-operating magnet assemblies 15 attached to the skull cap.

Further details regarding intermittent oscillatory stimulation and continuous oscillatory stimulation will now be discussed.

Intermittent Oscillatory Stimulation. In one preferred form of the invention, and looking now at FIG. 2A, computerized controller 25 is configured to operate magnet assemblies 15 so as to provide intermittent oscillatory stimulation. In this form of the invention, computerized controller 25 is configured to selectively cause a motor 45 of at least one of the magnet assemblies 15 to rotate the permanent magnet 50 of that magnet assembly so as to provide TMS to an individual, wherein computerized controller 25 causes the motor to rotate the permanent magnet for a stimulus period 56 of a given duration (e.g., 1-500 ms), wherein the stimulus period has a repetition rate of a given frequency 57 (e.g., 0.1-10 Hz), and wherein, during the stimulus period, the computerized controller causes the motor to rotate the permanent magnet at a particular rate of speed 58 (e.g., preferably no less than 400 Hertz). This mode of operation causes an actuated magnet assembly to provide a TMS stimulation pattern to the individual which consists of "packets" 59 of magnetic stimulation (i.e., the duration of which constitutes the "stimulus duration" 56) which are separated from one another by periods of substantial "quiet" 61 (i.e., the duration of such periods of quiet 61 constitutes the "repetition rate" 57 of the stimulus packets), wherein each of the "packets" 59 of magnetic stimulation consists of a series of discrete pulses 62 (i.e., the frequency of which, 58, reflects the rate of rotation of the magnet about the axis of the motor).

In essence, in this form of the invention, computerized controller 25 turns on the motor 50 of a magnet assembly 55, initiating the creation of a "packet" 59 of magnetic stimulation, thereafter turns off the motor of that magnet assembly so as to initiate a period of substantial "quiet" 61, thereafter turns on the motor again so as to create a subsequent "packet" 59 of magnetic stimulation, thereafter turns off the motor of that magnet assembly again so as to initiate a subsequent period of substantial "quiet" 61, etc.

Figure 2A:
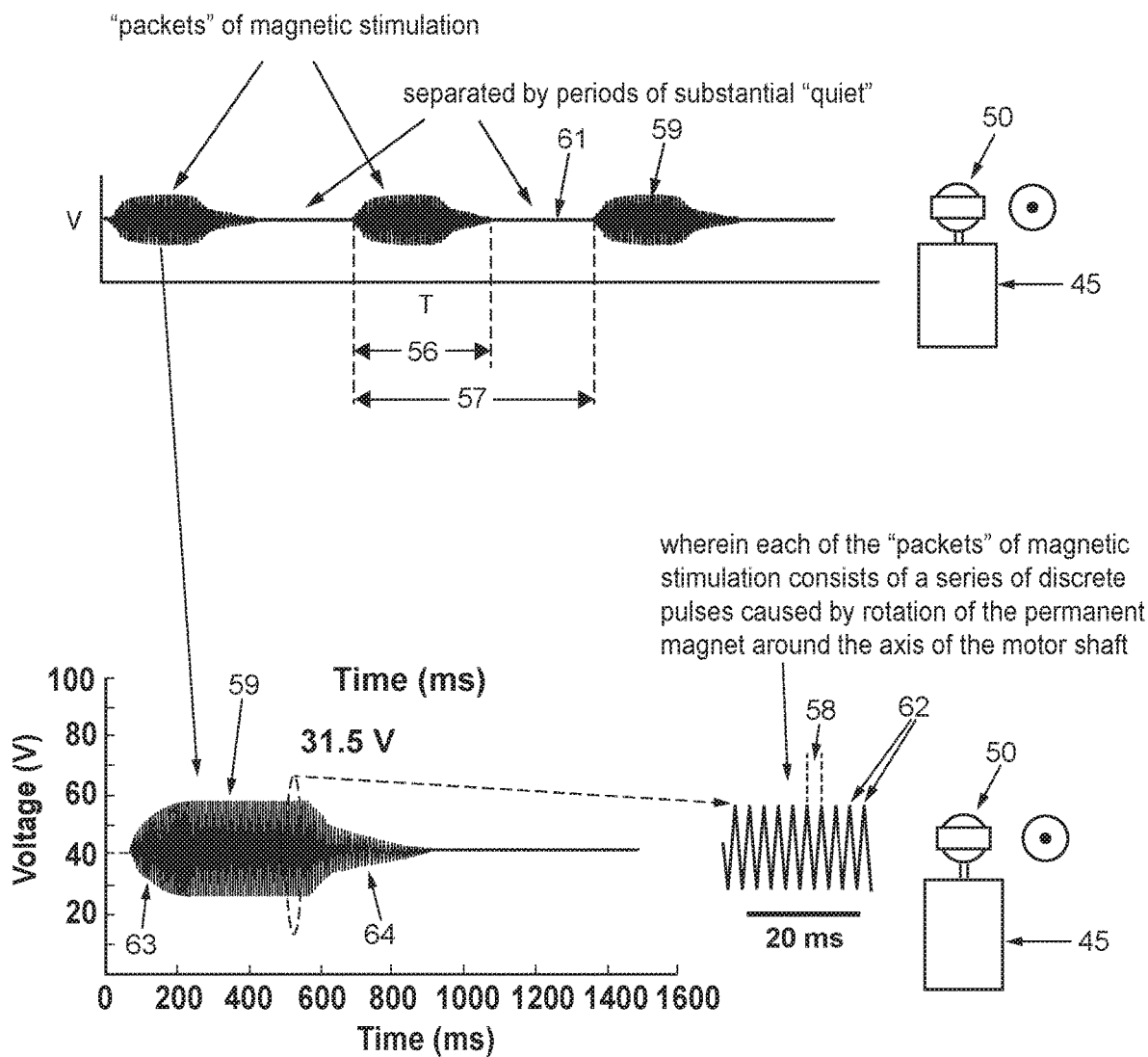
FIG. 2A is a schematic view showing a TMS stimulation pattern which comprises intermittent oscillatory stimulation, wherein "packets" of magnetic stimulation are separated by periods of substantial "quiet"

It will be appreciated that inasmuch as the starting and stopping of a motor may not be instantaneous, the leading and trailing portions of a "packet" 59 of magnetic stimulation may be tapered somewhat, e.g., such as is shown in FIG. 2A at 63 and 64, respectively.

Seen in a more global sense, each of the "packets" 59 of magnetic stimulation can themselves be considered to be "pulses" 59 of a given duration (i.e., the "stimulus duration" 56) separated by periods of "quiet" 61 and repeating with a given frequency 57 (i.e., the "repetition rate"). See also FIG. 3, which shows each of the "packets" 59 of magnetic stimulation as a single "pulse" 59 along a trace line.

Figure 3:
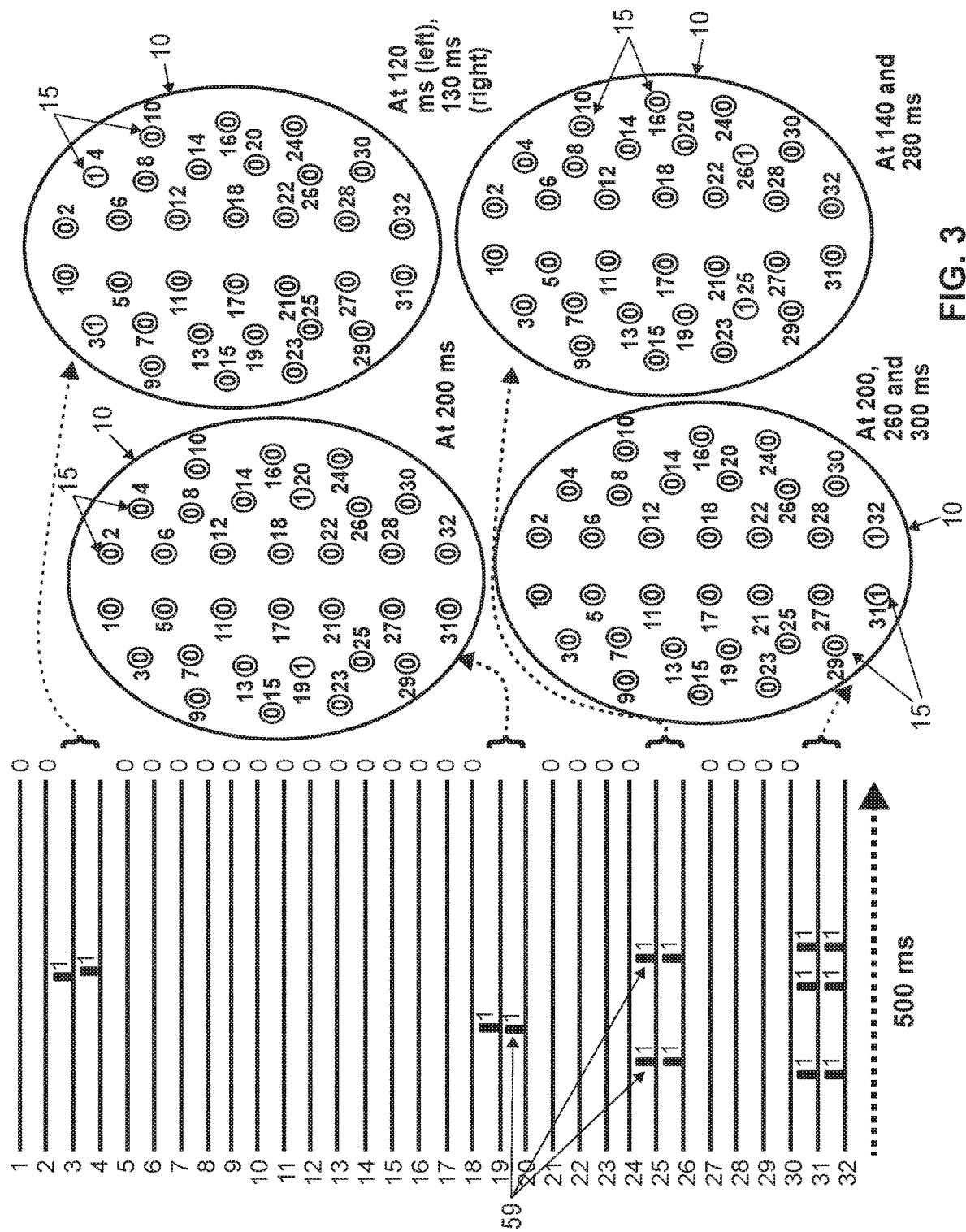
FIG. 3 is a schematic view illustrating how selective ones of the magnet assemblies of the TMS apparatus of FIGS. 1 and 2 may be activated at selected times so as to provide intermittent oscillatory stimulation TMS therapy to an individual, diagnostic testing and/or investigative protocol in neuroscience research.

In practice, and as also seen in FIG. 3, computerized controller 25 simultaneously coordinates the operation of numerous magnetic assemblies 15 so as to coordinate their respective pulses 59, whereby to apply the desired TMS stimulation to the individual.

Figure 3A:
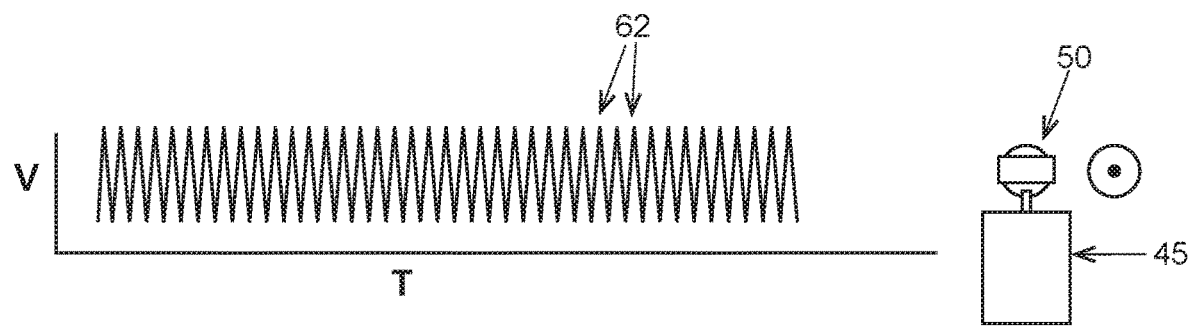
FIG. 3A is a schematic view showing a TMS stimulation pattern which comprises continuous oscillatory stimulation, wherein "wavy" stimuli are delivered throughout the duration of a stimulation session.
Figure 3B:
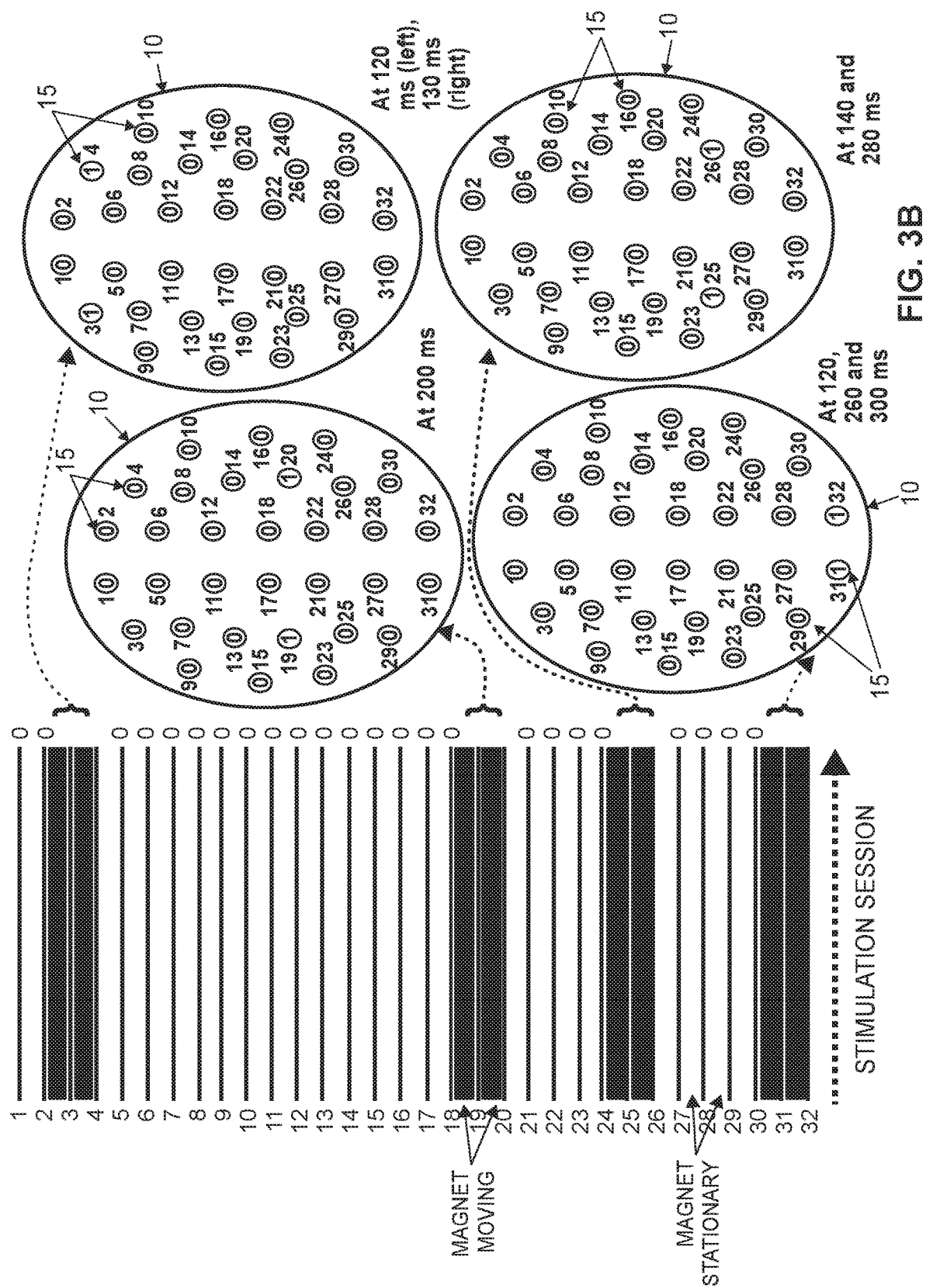
FIG. 3B is a schematic view illustrating how selective ones of the magnet assemblies of the TMS apparatus of FIGS. 1 and 2 may be activated at selected times so as to provide continuous oscillatory stimulation TMS therapy to an individual, diagnostic testing and/or investigative protocol in neuroscience research.

Continuous Oscillatory Stimulation. In another preferred form of the invention, and looking now at FIGS. 3A and 3B, computerized controller 25 is configured to operate magnet assemblies 15 so as to provide continuous oscillatory stimulation. In this form of the invention, computerized controller 25 is configured to selectively cause a motor 45 of at least one of the magnet assemblies 15 to rotate the permanent magnet 50 of that magnet assembly so as to provide TMS to an individual, wherein computerized controller 25 causes the motor to rotate in a continuous oscillatory manner, so that the "wavy" stimuli are delivered throughout the duration of a stimulation session that can last from a few seconds to several minutes. In one preferred form of the invention, the frequency of stimulus waves is approximately 400 Hz, although they may have a frequency higher or lower than 400 Hz. The frequency of the stimulus waves can be dynamically varied at fixed periodic or variable intervals using pulse width modulation with resultant variation in stimulus strength.

Thus, in accordance with the present invention, a clinician or investigator first determines, for each individual, (i) how many magnet assemblies 15 should be mounted to head mount 10, (ii) where those magnet assemblies 15 should be mounted on head mount 10, (iii) when various magnet assemblies 15 should have their permanent magnets 50 rotated, and (iv) the speed of such rotation, in order to precisely tailor the spatial, strength and temporal characteristics of the magnetic field which is generated by TMS apparatus 5, whereby to provide that individual with individual-specific TMS therapy, to assist in diagnosis and/or to map out brain function in neuroscience research.

Thereafter, when TMS therapy and/or testing is to be applied to the individual, the individual puts on head mount 10, the clinician or investigator mounts the appropriate number of magnet assemblies 15 to head mount 10, positioning those magnet assemblies at the appropriate locations on head mount 10, and then computerized controller 25 thereafter controls which magnet assemblies 15 have their magnets rotated when, and at what speed (i.e., computerized controller 25 thereafter controls which magnet assemblies 15 produce stimulation pulses 62 and the respective timing of those stimulation pulses 62 and, where the TMS therapy is to use intermittent oscillatory stimulation, the grouping of those stimulation pulses 62 and the separation between the grouping of those stimulation pulses 62). In this way, the spatial, strength and temporal characteristics of the magnetic field generated by TMS apparatus 5 can be precisely tailored according to each individual's needs, whereby to provide individual-specific TMS therapy to the individual, to assist in diagnosis and/or to map out brain function in neuroscience research.

See, for example, FIG. 3, which shows how selected magnet assemblies 15, located at various locations about head mount 10, may have their respective permanent magnets rotated at different times, i.e., so as to provide a desired spatially-tailored and temporally-tailored pulse pattern. In this respect it will be appreciated that as the permanent magnet of a particular magnetic assembly 15 is rotated, it will apply a rapidly changing magnetic field to the individual, and this changing magnetic field is a function of the size and strength of the permanent magnet 50 of that magnet assembly and the rate at which the permanent magnet is rotated.

Figure 4:
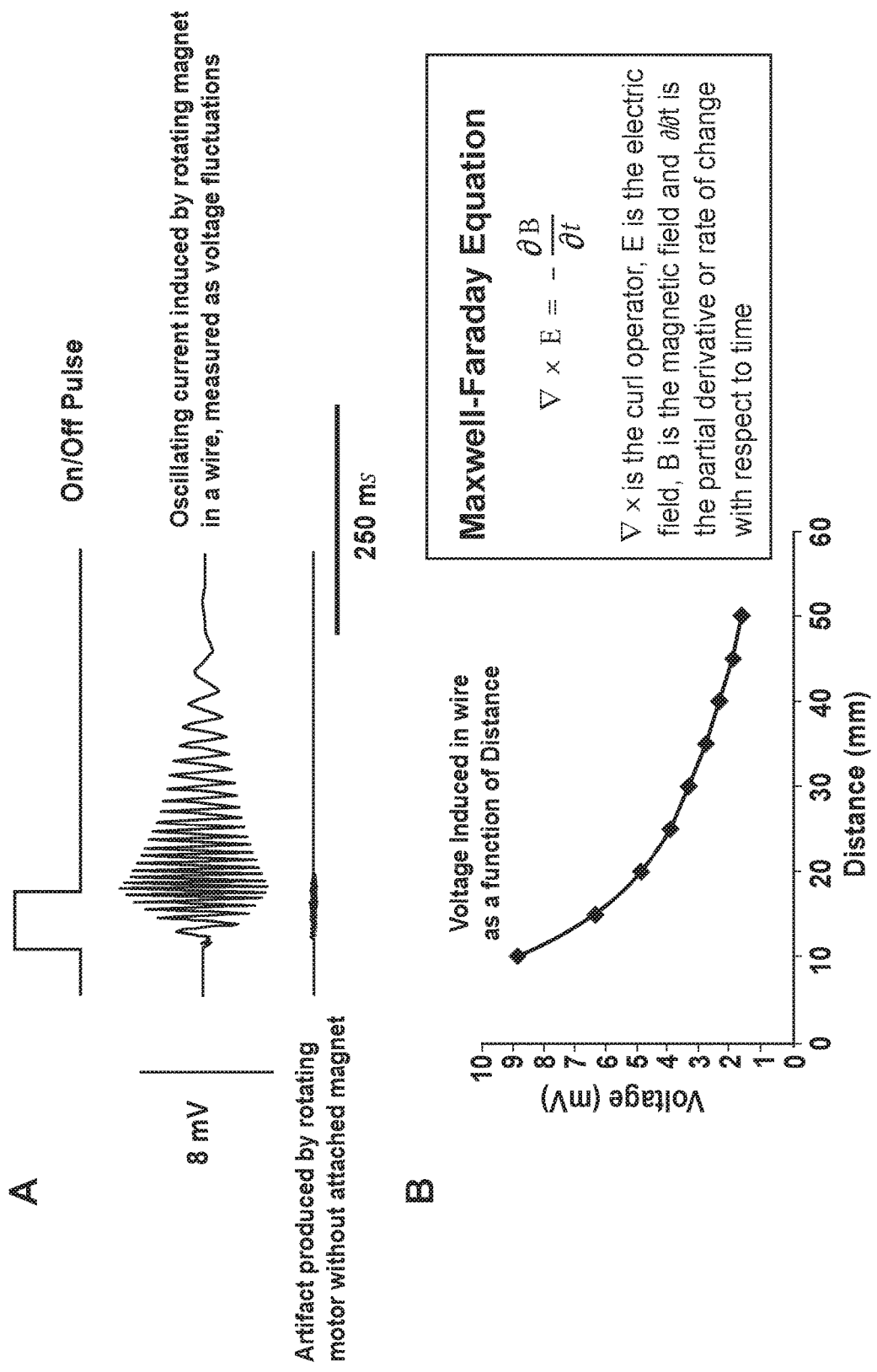
FIG. 4 is a schematic view illustrating the physics of magnetic stimulation in a conductor.
Figure 5:
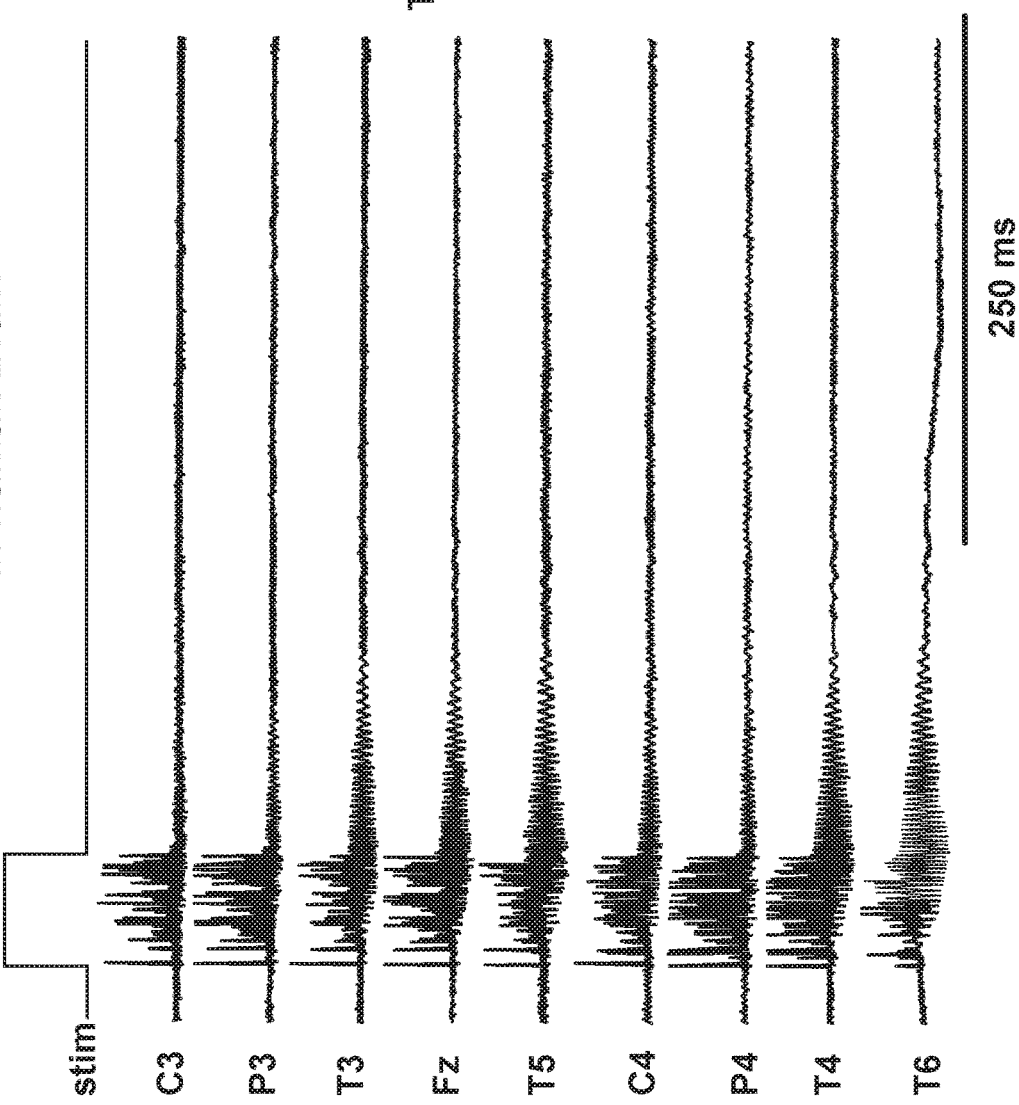
FIG. 5 is a schematic view illustrating the biophysics of magnetic stimulation of a brain.
Figure 6A:
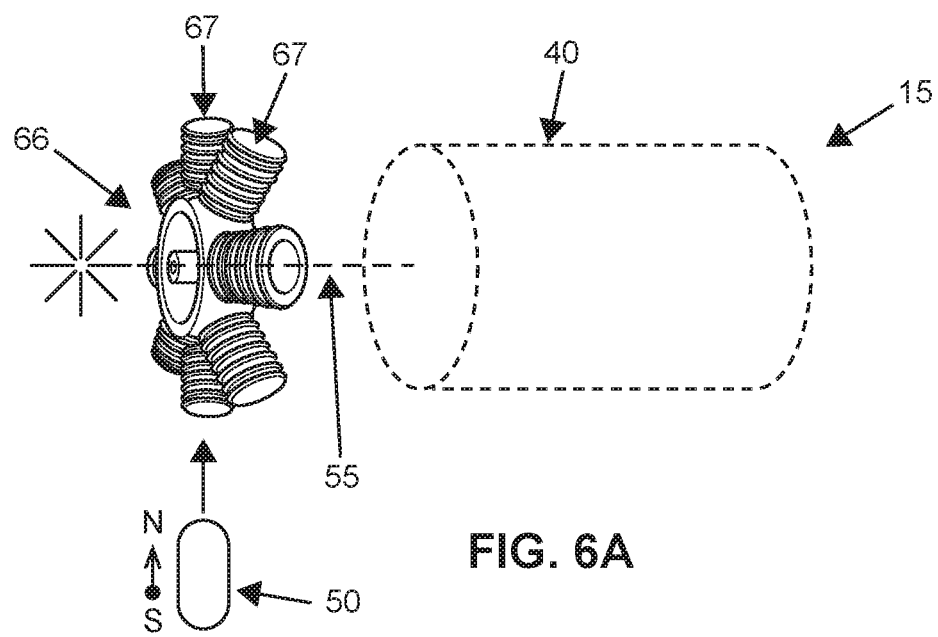
FIG. 6A is a schematic view illustrating a spoked wheel for mounting one or more magnets to the drive shaft of a motor.
Figure 6B:
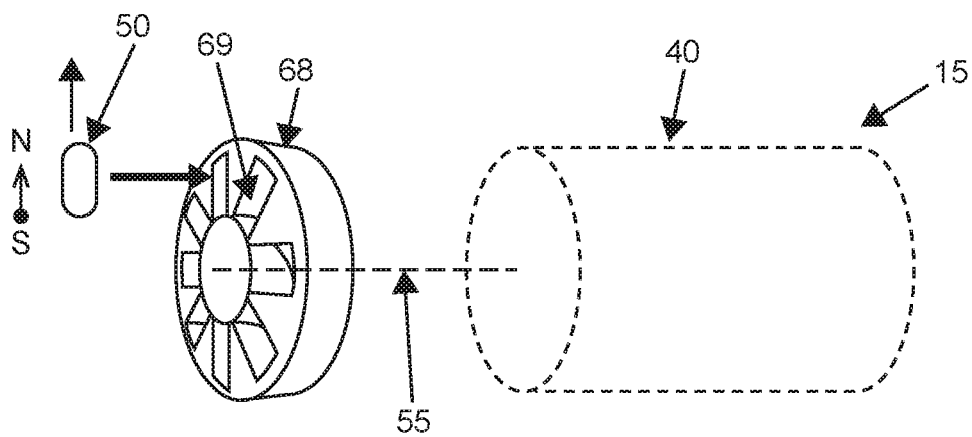
FIGS. 6B and 6C are schematic views illustrating slotted wheels for mounting one or more magnets to the drive shaft of a motor.
Figure 6C:
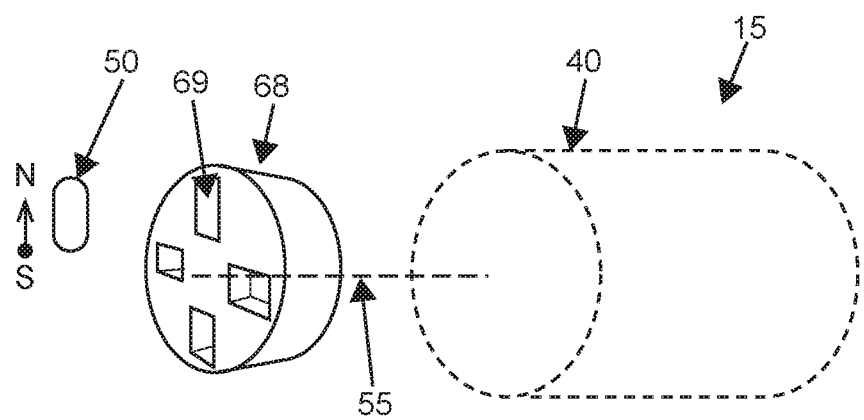
Figure 6D:
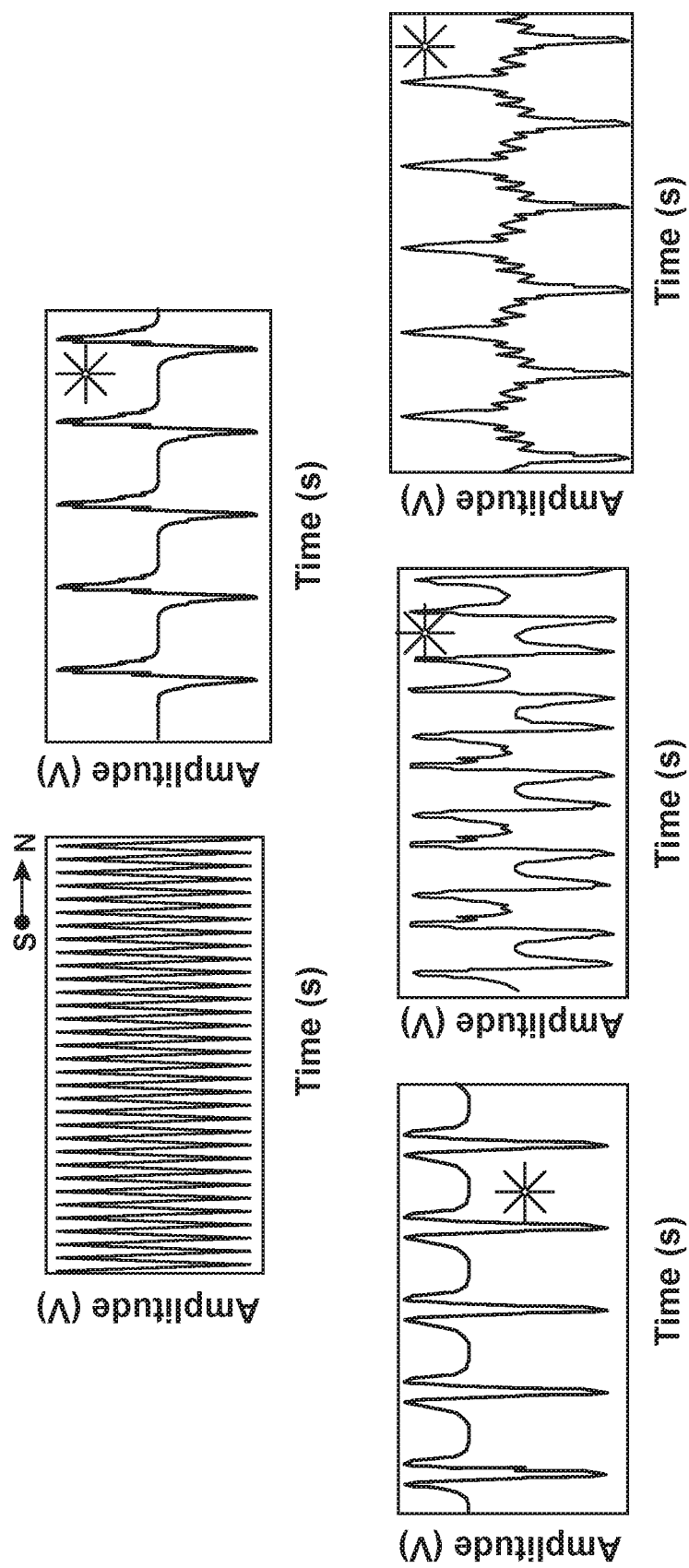
FIG. 6D is a schematic view illustrating various stimulation patterns which may be produced with the constructions shown in FIGS. 6A-6C.

See also, for example, FIG. 4, which illustrates the physics of magnetic stimulation in a conductor, and FIG. 5, which illustrates the rapid voltage fluctuations recorded during magnetic stimulation of a single site on the head of an individual (note that the electrical responses shown in FIG. 5 may also include electrical responses in the electrode wires).

Furthermore, it will be appreciated that the rapidly changing magnetic fields produced by the plurality of magnetic assemblies 15 located on head mount 10 together aggregate into a complex, composite, rapidly changing magnetic field which varies across the brain of the individual, both spatially and temporally, according to the positions of the magnet assemblies 15 on head mount 10 and the relative timings of their respective magnet rotations.

Thus it will be seen that with the novel TMS apparatus 5 of the present invention, the clinician or investigator may custom tailor the spatial, strength and temporal characteristics of the magnetic field generated by the TMS apparatus 5 for each individual, whereby to provide individual-specific TMS therapy, to assist in diagnosis and/or to map out brain function in neuroscience research.

Significantly, the present invention comprises a portable, wearable device that can be used outside of a medical or research facility, e.g., at home. Furthermore, individuals can self-administer a prescribed treatment regimen at home through handheld, or worn, wired or wireless electronic controllers.

It should be appreciated that, inasmuch as the present invention comprises multiple magnetic stimulators directable at multiple brain structures, it can be possible to achieve better treatment, diagnostic testing and/or insight into brain function through its use in neuroscience research.

Also, inasmuch as the present invention comprises multiple magnetic stimulators directable at a single brain structure, it can be possible to achieve superior results because they can induce current flow in multiple orientations.

Furthermore, inasmuch as the present invention comprises multiple magnetic stimulators which can aggregate their magnetic fields for more robust brain stimulation, it can be possible to achieve better treatment, diagnostic testing and/or insight into brain function through its use in neuroscience research. Among other things, this more robust brain stimulation can relate to which regions of the brain are stimulated, the orientation(s) of the current flow induced in the regions which are stimulated, the magnitudes of the current flow induced in the regions which are stimulated, and the timings of such stimulation.

In accordance with the present invention, there is also provided a novel method for determining how many magnet assemblies 15 should be mounted to head mount 10, where those magnet assemblies 15 should be mounted on head mount 10, when various magnet assemblies 15 should have their magnets rotated, and the speed of such magnet rotation, in order to precisely tailor the spatial, strength and temporal characteristics of the magnetic field which is to be applied to that individual, whereby to provide that individual with individual-specific TMS therapy, to assist in diagnosis and/or to map out brain function in neuroscience research. More particularly, in accordance with the present invention, head mount 10 may include a plurality of electrodes 60 for monitoring changes in the electrical activity of the brain of the individual. Electrodes 60 are preferably connected to computerized controller 25 so that changes in the electrical activity of the brain, monitored by electrodes 60, can be correlated with variations in the spatial, strength and temporal characteristics of the magnetic field being applied to the individual by TMS apparatus 5, which in turn corresponds to the number, location and speed of rotation of the various magnet assemblies 15. In this way, using a feedback process, changes in the number, location and speed of rotation of the various magnet assemblies 15 can be correlated to changes in the electrical activity of the brain of the individual, whereby to create an individual specific TMS therapy, to assist in diagnosis and/or to map out brain function in neuroscience research.

The present invention offers numerous advantages over the prior art. More particularly, the novel TMS apparatus 5 of the present invention allows the spatial, strength and temporal characteristics of the magnetic field to be custom tailored for each individual, whereby to provide individual-specific TMS therapy, to assist in diagnosis and/or to map out brain function in neuroscience research. Among other things, the present invention provides the following significant advantages over conventional TMS: (i) it comprises a portable, wearable device that can be used outside of a medical or research facility, e.g., at home; (ii) individuals can self-administer a prescribed treatment regimen at home through handheld, or worn, wired or wireless electronic controllers; (iii) it comprises multiple magnetic stimulators directable at multiple brain structures which can lead to better treatment, diagnostic testing and/or insight into brain function through its use in neuroscience research; (iv) it comprises multiple magnetic stimulators directable at a particular brain structure which can be more effective because they can induce current flow in multiple orientations; and (v) it comprises multiple magnetic stimulators which can aggregate their magnetic fields for more robust brain stimulation. In addition, the present invention eliminates the risk of accidental injury to the individual through electric shocks, burns, seizures, etc.

See FIG. 6, which lists some of the advantages of the present invention over conventional TMS apparatus.

Additional Constructions

If desired, the entire outer surface of head mount 10 may be covered by a single large fastener base 35, or major sections of head mount 10 may be covered by several large fastener bases 35, where the one or more large fastener bases 35 receive one or more magnet assemblies 15.

Furthermore, if desired, head mount 10 may be formed as a harness, comprising a plurality of straps which are connected together, but have spacing between the various straps, so as to provide a grid-like structure about the head. These straps can be formed out of leather, plastic, a textile, etc. In this form of the invention, fastener bases 35, and hence magnet assemblies 15, are mounted along the straps which make up head mount 10.

It is also possible to mount multiple magnets to the drive shaft of a single motor. By way of example but not limitation, and looking now at FIG. 6A, a "spoked wheel" 66 may be mounted to the drive shaft 55 of a motor 40 of a magnet assembly 15, wherein the spoked wheel 66 comprises a plurality of seats 67 (e.g., eight seats 67) to receive magnets 50. It will be appreciated that all of seats 67 may receive magnets 50 or only some of the seats 67 may receive magnets 50. Furthermore, specific ones of the magnets 50 may be mounted within seats 67 so that their N-pole faces the drive shaft 55, or specific ones of the magnets 50 may be mounted within seats 67 so that their S-pole faces the drive shaft 55. By way of further example but not limitation, and looking now at FIG. 6B, a "slotted wheel" 68 may be mounted to the drive shaft 55 of a motor 40 of a magnet assembly 15, wherein the slotted wheel 68 comprises a plurality of seats 69 (e.g., eight seats 69) to receive magnets 50. Again, it will be appreciated that all of seats 69 may receive magnets 50 or only some of the seats 69 may receive magnets 50. Furthermore, specific ones of the magnets 50 may be mounted within seats 69 so that their N-pole faces the drive shaft 55, or specific ones of the magnets 50 may be mounted within seats 69 so that their S-pole faces the drive shaft 55. It will be appreciated that the number of seats 67 provided in spoked wheels 66, and/or the number of seats 69 provided in slotted wheels 68 may be varied. See, for example, FIG. 6C, which shows four seats 69 formed in slotted wheel 68.

In one preferred form of the invention, 8 seats 67 are provided in spoked wheel 66, and 8 seats 69 are provided in slotted wheels 68, so that magnets 50 may be oriented radially at 45 degree angles with respect to each other (where adjacent seats 67, or adjacent seats 69, are filled with magnets).

It will be appreciated that spoked wheels 66 and slotted wheels 68 enable the user to change the shapes of the stimulus waves provided by magnet assemblies 15, e.g., such as to better mimic different neuronal bursting patterns. See, for example, FIG. 6D, which shows a variety of different stimulus patterns which may be provided using spoked wheels 66 and/or slotted wheels 68. Some multiple magnet configurations can result in up to 3-fold greater stimulus strengths without any increase in motor rotation speed.

The spoked wheels 66 and/or the slotted wheels 68 may be made of strong, light plastic and 3D-printed with high precision. Note that where a seat 67 of spoked wheel 66 is not filled with a magnet 50, and/or where a seat 69 of slotted wheel 68 is not filled with a magnet 50, a non-magnetized metal rod (of the same shape, size and weight as magnets 50) are preferably positioned in the "unfilled" seats 67, 69 so as to keep the spoked wheel or slotted wheel balanced. Caps (not shown) are preferably provided to keep magnets 50 (and any non-magnetized metal rods) secured in seats 67, 69.

It will be appreciated that the arrangement of the magnets and non-magnetized rods can be changed in any specified manner. Similarly, the orientation of the poles of the magnets can also be changed. These changes enable the shape of repeated waves of stimulation to be varied correspondingly when the component is rotated by the motor. The varied positions of the magnets also allow the rise times, and consequently the amplitude, of the stimuli to be varied various ways. The overall magnetic field configuration varies based on the arrangements and orientations of the magnets, producing up to 3-fold greater stimulus strengths for some configurations. Mixing and matching of up to 8 magnets, each in two different orientations, and non-magnetic rods at different positions in the wheel, generate a repertoire of 834 different shapes of stimulus waves (see FIG. 6D for various examples).

Figure 7:
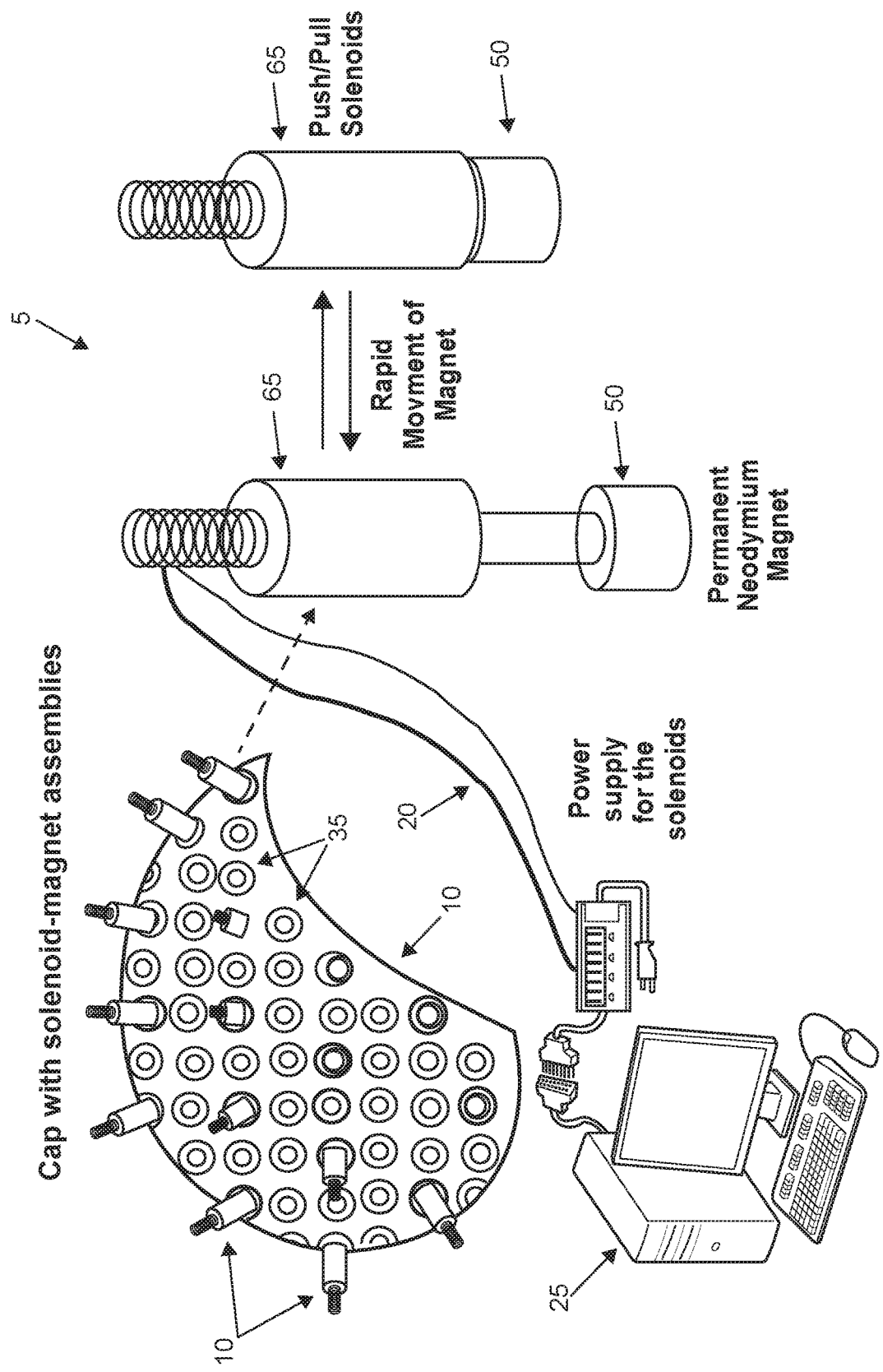
FIG. 7 is a schematic view illustrating alternative apparatus for providing TMS to an individual.

In addition, if desired, magnet assemblies 15 may be constructed so that magnets 50 are moved longitudinally, rather than rotationally, by actuators (e.g., linear actuators) in order to produce a rapidly changing magnetic field. See, for example, FIG. 7, where the actuators comprise solenoids 65 to move magnets 50 rapidly so as to create the changing magnetic field utilized in the present invention.

Also, if desired, permanent magnets 50 may be replaced by small electromagnets, if the requisite high strength magnetic field can be achieved (e.g., so as to provide a rapid change of magnetic flux of at least 500-600 Tesla/second), and with the appropriate amount of cooling to prevent heating and melting of the magnet coils.

In accordance with the present invention, it is also possible to provide a head mount 10 (e.g., a skull cap) which has a predetermined number of magnet assemblies 15 already mounted on (or incorporated into) head mount 10 in a predetermined pattern. In this case, the clinician determines which ones of the predetermined, predisposed magnet assemblies 15 should be activated and, for those magnet assemblies which are to be activated, when they should have their magnets rotated, and the speed of such rotation, in order to precisely tailor the spatial, strength and temporal characteristics of the magnetic field which is to be applied to the individual, whereby to provide that individual with individual specific TMS therapy, to assist in diagnosis, and/or to map out brain function in neuroscience research. Furthermore, in this form of the invention, it may be desirable to provide a kit of such devices, wherein each device in the kit comprises a head mount 10 (e.g., a skull cap) which has a predetermined number of magnet assemblies 15 already mounted on (or incorporated into) head mount 10 in a predetermined pattern, with each device in the kit providing a different predetermined pattern of magnet assemblies 15.

System Using High-Speed Shutters to Further Tailor the Magnetic Stimuli

In the foregoing, there is disclosed a novel method and apparatus for providing transcranial magnetic stimulation (TMS) to the brain of an individual so as to induce, modulate and/or disrupt neural activity in the brain of the individual.

In one form of the invention, the apparatus comprises a plurality of high strength (e.g., 1.48 Tesla) neodymium magnets, each attached to a high speed motor (or actuator). These magnet assemblies are mounted in various locations on a EEG-type cap or head mount. The magnet assemblies are interfaced with a computer, and a software program having a user-friendly graphical user interface enables dynamic interaction with the apparatus by a physician, technician, researcher and/or the individual themselves. On account of its construction, the apparatus is able to provide tailored magnetic stimulation to the brain, with the magnetic stimulation being tailored according to (i) where the magnet assemblies are located on the EEG-type cap, (ii) which specific magnet assemblies are energized (e.g., which magnets are rotated by their associated motors) and when (i.e., so as to spatially and temporally tailor the pulses 62 produced by the magnet assemblies), and (iii) at what speed each magnet is rotated by its associated motor. The apparatus is of use in studying brain function in neuroscience research, and potentially in the diagnosis and/or treatment of various neuropsychiatric conditions such as depression, stroke rehabilitation, chronic pain and neurodegenerative diseases.

The novel method and apparatus of the present invention provides significant advantages over traditional approaches for providing Transcranial Magnetic Stimulation (TMS). More particularly, traditional TMS devices utilize a large coil (i.e., an electromagnet) placed on the surface of the head of the individual. The present invention's use of a plurality of small but powerful permanent magnets, each independently positionable and independently rotatable, enable the apparatus of the present invention to generate a magnetic field which is both time-varying (e.g., by varying the duration and timing of rapid rotation of the magnets) and spatially-varying (by selecting which magnets are rotated) and strength-varying (by selecting the speed of rotation of the magnets).

A comparison of the magnetic fields generated by the permanent magnets of the present invention vis-à-vis the typical peak fields of conventional TMS coils has shown that whereas the penetration depth of conventional TMS coils is greater than that of the permanent magnets of the present invention, the permanent magnet fields of the present invention are more localized. The pulse rise time, an equally important factor for the amplitude of induced voltages and penetration depth, can potentially be made comparable by using ultra-fast motors to move the permanent magnets of the present invention.

Furthermore, by using motors which have very short start and stop delays, when using intermittent oscillatory stimulation, the stimulation "packets" 59 can have reduced tapering at their beginnings and ends 63 and 64, respectively. In other words, each of the pulses (packets) 59 can appear more like a "square" wave than a rising/falling wave.

The feasibility of the permanent magnet approach of the present invention has been demonstrated by mapping motor areas in humans by recording the electromyographic response of the thenar muscle. Thenar induced motor unit potentials were maximized for individually fixed stimulus locations and fell off for stimulation at a distance of 10 mm away from the peak location, indicating the focusing properties of the mild stimuli. Significantly, the present invention's provision of TMS with permanent magnets, arranged in an array of independent stimulation sites across the cortex, allows for investigations of interdependencies and spatiotemporal or synchronous modulation of cortical networks of varying sizes.

It will be appreciated that the novel method and apparatus discussed above depends on the provision of a plurality of rapidly-moving, high-strength permanent magnets, positioned and energized (i.e., started and stopped) as appropriate, so as to deliver the desired magnetic stimuli to the brain.

In accordance with the present invention, there is now provided an additional construction which provides an additional mode of tailoring the magnetic stimuli applied to the brain of the individual. This new construction is particularly useful where intermittent oscillatory stimulation is to be applied, since it provides a way to tailor the stimulation packets 59 without requiring the motor of a magnet assembly to be started and stopped. More particularly, this new construction involves rapid unshielding and shielding of the magnetic fields of the permanent magnets using a magnetic shield shutter mechanism. The magnetic shield shutter mechanism is preferably formed either by using high-speed shutters formed out of a special magnetic shielding material or by transiently changing the efficacy of a special magnetic shielding material, wherein the high-speed shutters or the transiently-changing shielding material is interposed between permanent magnets and the brain of the individual.

Significantly, the magnetic shield shutter mechanism of the present invention is configured to modulate the magnetic fields of the permanent magnets, and hence permits stationary or moving permanent magnets to be used with the present invention. This is in contrast to embodiments where no magnetic shield shutter mechanism is provided, and hence require the use of moving permanent magnets to create the changing magnetic fields applied to the anatomy. More particularly, where the permanent magnets are moving, and hence creating a changing magnetic field by virtue of magnet movement, the magnetic shield shutter mechanism can be used to further modulate the changing magnetic field created by the moving magnet. Correspondingly, where the permanent magnets are not moving, and hence provide a static magnetic field, the magnetic shield shutter mechanism can be used to modulate the static magnetic field provided by the stationary permanent magnet and hence provide the desired changing magnetic field at an anatomical location. Thus, the magnetic shield shutter mechanism of the present invention allows either stationary or permanent magnets to be used in the magnet assemblies attached to head mount 10.

Significantly, the magnetic shield shutter mechanism also provides another way of tailoring the stimulation pulses 59 (i.e., stimulation "packets" 59) without requiring the motor of a magnet assembly to be started and stopped. More particularly, in this form of the invention, a motor of a magnet assembly can be run continuously, and the beginning 63 and end 64 of a stimulation "packet" 59 can be established by appropriate operation of the magnetic shield shutter mechanism.

By way of example but not limitation, in one form of the invention, the magnet assembly may comprise a moving permanent magnet to provide the desired changing magnetic field and the magnetic shield shutter mechanism may be omitted; in another form of the invention, the magnet assembly may comprise a stationary permanent magnet and the magnetic shield shutter mechanism may be used to provide the desired changing magnetic field; and in another form of the invention, the magnet assembly may comprise a moving permanent magnet to provide a changing magnetic field and the magnetic shield shutter mechanism may be used to modulate the changing magnetic field created by the moving magnet so as to provide a desired changing magnetic field at the anatomical location.

Also, if desired, the permanent magnets may be replaced by small electromagnets, if the requisite high strength magnetic field can be achieved (e.g., so as to provide a rapid change of magnetic flux of at least 500-600 Tesla/second), and with the appropriate amount of cooling to prevent heating and melting of the magnet coils. Thus, by way of example but not limitation, in one form of the invention, the magnet assembly may comprise a moving electromagnet to provide the desired changing magnetic field and the magnetic shield shutter mechanism may be omitted; in another form of the invention, the magnet assembly may comprise a stationary electromagnet and the magnetic shield shutter mechanism may be used to provide the desired changing magnetic field; and in another form of the invention, the magnet assembly may comprise a moving electromagnet to provide a changing magnetic field and the magnetic shield shutter mechanism may be used to modulate the changing magnetic field created by the moving magnet so as to provide a desired changing magnetic field at the anatomical location.

In one preferred form of the present invention, each magnet assembly 15 is provided with an associated magnetic shield shutter mechanism for additionally tailoring the magnetic stimuli applied to the brain of the individual by that magnet assembly 15. And in one preferred form of the present invention, each magnet assembly 15 and its associated magnetic shield shutter mechanism are configured as a unit, such that when that magnet assembly 15 is mounted to head mount 10, its associated magnetic shield shutter mechanism is also mounted to head mount 10.

Figure 8:
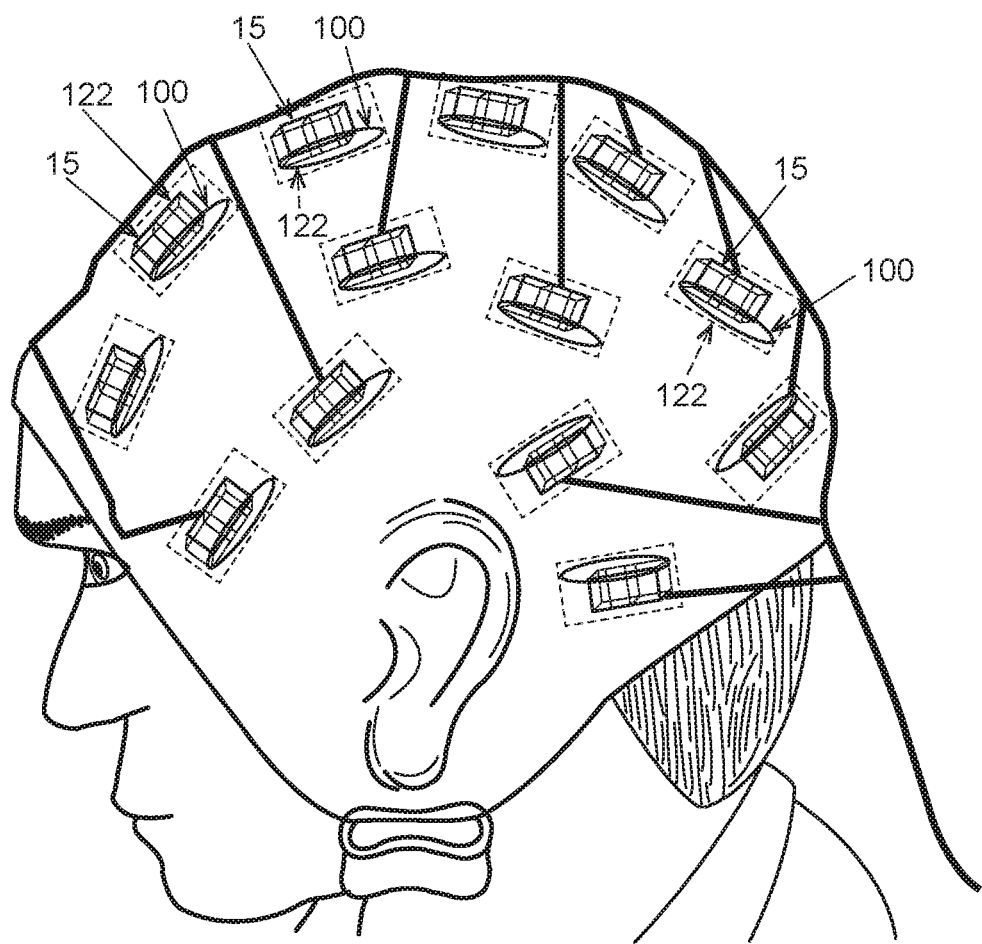
FIGS. 8 and 9 are schematic views illustrating novel apparatus for providing TMS to an individual, wherein the magnet assemblies comprise magnet shield shutter mechanisms for tailoring the magnetic stimuli applied to the brain of an individual.
Figure 9:
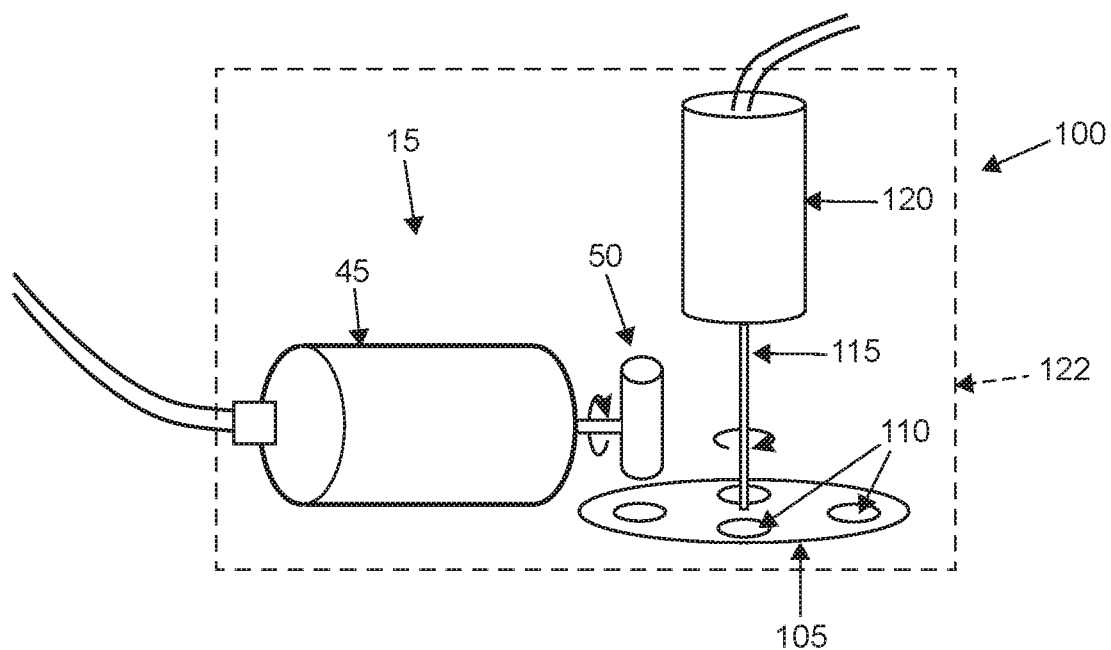

More particularly, and looking now at FIGS. 8 and 9, in one form of the present invention, there is provided a magnet shield shutter mechanism 100 which comprises a disc 105 formed out of a magnetic shielding material. By way of example but not limitation, disc 105 may be formed out of Mu-Metal, a nickel-iron alloy composed of approximately 77% nickel, 16% iron, 5% copper and 2% chromium or molybdenum. By way of further example but not limitation, disc 105 may be formed out of MagnetShield, a magnetic shield plate available from AdrProVita of Baltimore, Md., USA. Disc 105 has at least one circular opening 110 formed therein. Disc 105 is disposed between stationary or moving magnet 50 of a magnet assembly 15 and the brain of the individual. Disc 105 is mounted to the drive shaft 115 of a motor 120, such that motor 120 can be used to selectively (i) position the magnetic shielding material of disc 105 between stationary or moving magnet 50 and the brain of the individual, whereby to shield the brain of the individual from the magnetic field of the stationary or moving magnet 50, or (ii) position the at least one circular opening 110 between stationary or moving magnet 50 and the brain of the individual, whereby to expose the brain of the individual to the magnetic field of stationary or moving magnet 50, or (iii) sweep the at least one circular opening 110 of disc 105 by stationary or moving magnet 50 so as to modulate the magnetic field created by magnet 50 (i.e., to modulate the static magnetic field of a stationary magnet 50 so as to create the desired changing magnetic field or to modulate the changing magnetic field of a moving magnet 50 so as to create the desired changing magnetic field). Motor 120 is used to appropriately positioning a desired portion of disc 105 between stationary or moving magnet 50 and the brain of the individual. Preferably motor 120 is controlled by the same computerized controller 25 which drives magnet assemblies 15.

As seen in FIGS. 8 and 9, magnet assembly 15 and its associated magnetic shield shutter mechanism 100 are preferably configured as a unit, with magnet assembly 15 and its associated magnetic shield shutter mechanism 100 being contained in a housing 122, such that when that magnet assembly 15 is mounted to head mount 10 (e.g., by mounting housing 122 to head mount 10), its associated magnetic shield shutter mechanism is also mounted to head mount 10.

Figure 10:
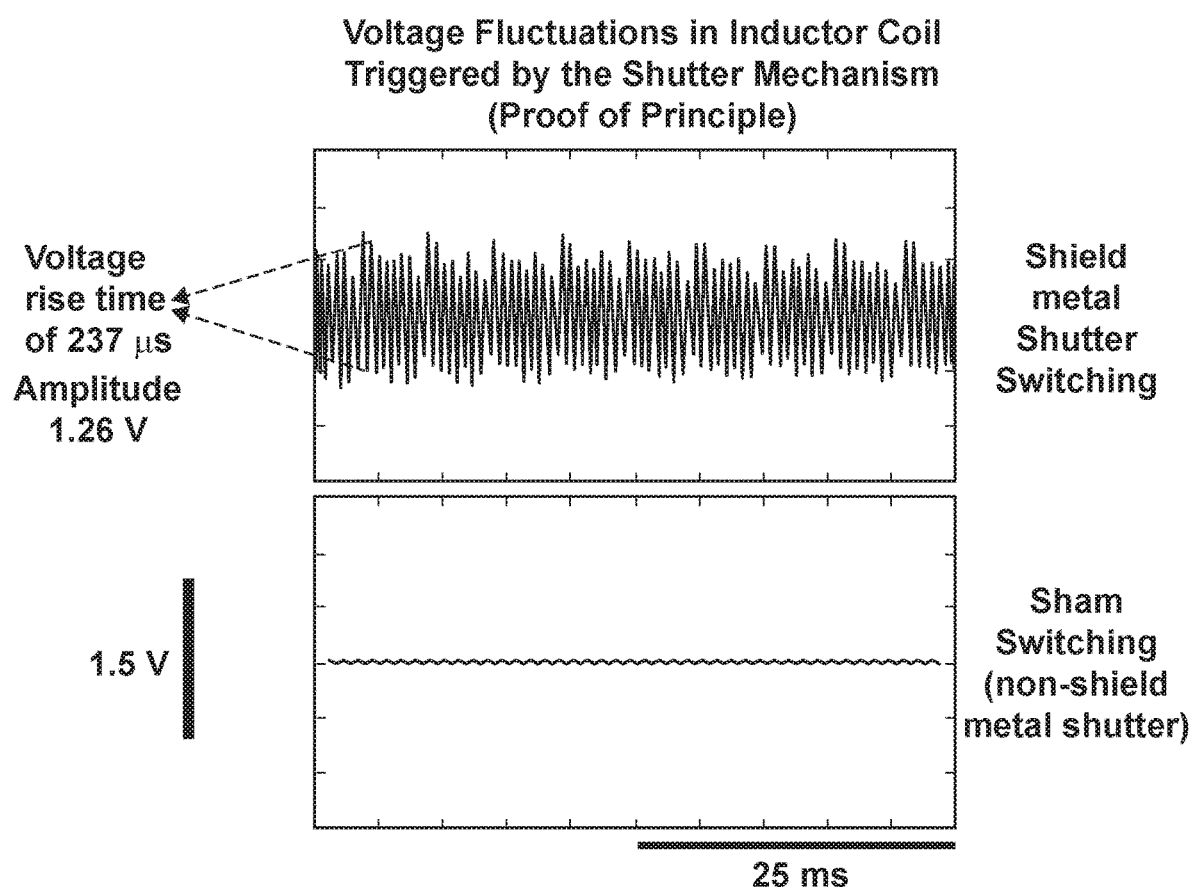
FIG. 10 is a schematic view illustrating voltage fluctuations created through the use of the magnet shield shutter mechanism shown in FIGS. 8 and 9.

FIG. 10 shows how the magnetic field of a magnet assembly 15 may be tailored by the magnetic shield shutter mechanism 100 of FIGS. 8 and 9.

Figure 11:
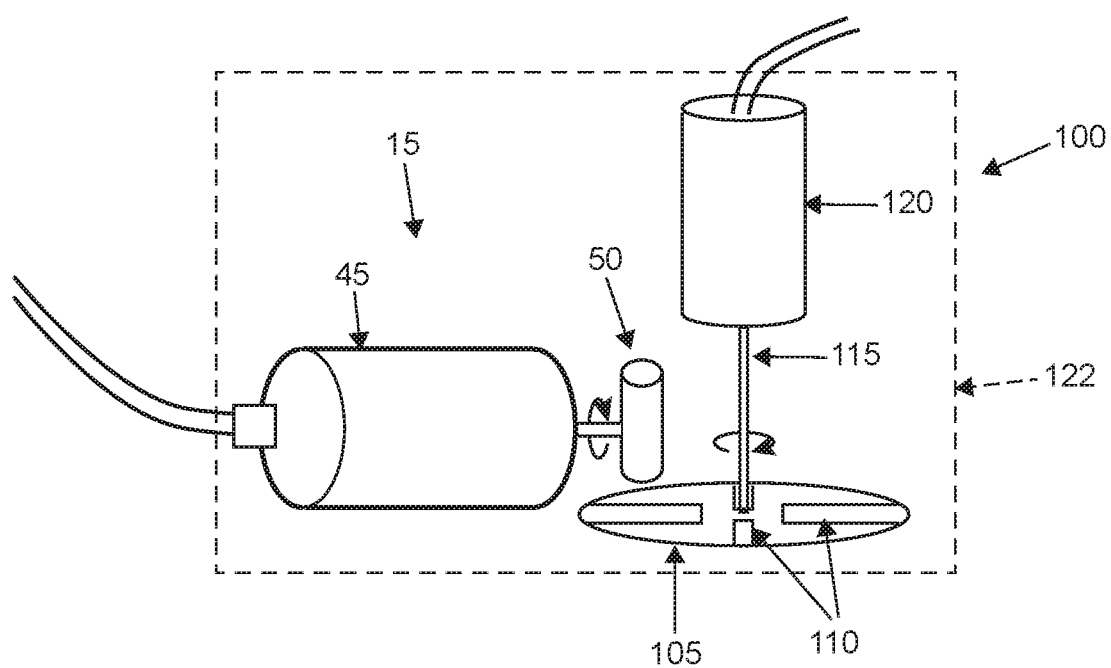
FIG. 11 is a schematic view illustrating another form of magnet shield shutter mechanism.

If desired, and looking now at FIG. 11, the at least one circular opening 110 may be replaced by at least one slot 110. Alternatively, the at least one circular opening 110 may be replaced by at least one opening of another configuration.

In another form of the present invention, and looking now at FIG. 12, the magnet shield shutter mechanism 100 comprises a shielding material 125 whose magnetic permeability and/or saturation may be rapidly and transiently changed by an electrically-triggered mechanism so as to effectively provide a shutter mechanism, whereby to allow tailoring of the magnetic stimulus delivered to the individual. See, for example, Sanchez et al., 2011, Antimagnets: controlling magnetic fields with superconductor-metamaterial hybrids, New J. Phys., 13, 093034, doi:10.1088/1367-2630/13/9/093034, which discusses shielding material whose magnetic permeability and/or saturation may be rapidly and transiently changed by an electrically-triggered mechanism. In this form of the invention, the transiently-changing shielding material is disposed between stationary or moving magnet 50 and the brain of the individual so as to modulate the magnetic field created by magnet 50 (i.e., to modulate the static magnetic field of a stationary magnet 50 so as to create the desired changing magnetic field or to modulate the changing magnetic field of a moving magnet 50 so as to create the desired changing magnetic field). When the brain of the individual is to be shielded from the magnetic field of stationary or moving magnet 50, the magnetic permeability and/or saturation of shielding material 125 is reduced. Correspondingly, when the brain of the individual is to be exposed to the magnetic field of stationary or moving magnet 50, the magnetic permeability and/or saturation of the shielding material 125 is increased. The electrically-triggered mechanism is preferably controlled by the same computerized controller 25 which drives the magnet assemblies 15.

As seen in FIG. 12, magnet assembly 15 and its associated magnetic shield shutter mechanism 100 are preferably configured as a unit, with magnet assembly 15 and its associated magnetic shield shutter mechanism 100 being contained in housing 122, such that when that magnet assembly 15 is mounted to head mount 10 (e.g., by mounting housing 122 to head mount 10), its associated magnetic shield shutter mechanism is also mounted to head mount 10.

The provision of high-speed shutters in conjunction with the magnet assemblies 15 increases the functionality, capability and efficiency of the apparatus. Among other things, it allows single pulses 59 of magnetic stimulation with sub-millisecond rise times to be delivered to the brain, thereby making it possible to more accurately measure the delays in onset of responses to the magnetic stimuli in research and diagnostic settings. One specific diagnostic application of the new method would be the measurement of electromyographic induced motor unit potential responses from different muscle groups, and induced responses from different locations on the scalp and spinal column, upon serial multi-site stimulation of the motor cortex, to assess the functional integrity of the corticospinal tract, and assist in the differential diagnosis of upper and/or lower motor neuronal dysfunctions such as Amyotrophic Lateral Sclerosis. The new method also enables more flexibility and control of the stimulus protocol in potential therapeutic applications.

The rapid stimulus delivery can also have diagnostic and therapeutic application for stimulation of pathways and structures other than the brain with single magnet-shutter assemblies. These stimulation sites may include the spinal cord and peripheral nerves and muscles.

Changing the Orientation of the Rotating Permanent Magnet Using a Servomotor Mechanism In some situations it may be desirable to precisely adjust the orientation of magnet assemblies 15, e.g., so as to match the direction of nerve cells/fibers in the cortex and/or to further tailor the magnetic field applied to the anatomy by a specific magnet assembly and/or to further tailor the aggregated magnetic field applied to the anatomy by the various magnet assemblies attached to head mount 10. This may be effected to some extent by adjusting the disposition of magnet assemblies 15 on head mount 10, however, in some circumstances it may not be possible to achieve the desired precision in orientation, e.g., due to limitations in the manner in which fastener connect 40 on magnet assemblies 15 mate with fastener base 35 on head mount 10. To this end, and looking now at FIG. 13, motor 45 (for turning permanent magnet 50) may be mounted on the shaft 126 of a servomotor 127, such that activating servomotor 127 can allow the axis of rotation of the moving magnet 50 to be precisely and dynamically changed, e.g., without moving housing 122 on head mount 10.

Modifications of the Preferred Embodiments

It should be appreciated that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for applying Transcranial Magnetic Stimulation (TMS) to the brain of an individual, wherein the apparatus comprises:
   a head mount for disposition on the head of an individual;
   a plurality of magnet assemblies for releasable mounting on the head mount, wherein each of the magnet assemblies comprises a permanent magnet, and at least one of (i) a movement mechanism for moving the permanent magnet and/or (ii) a magnetic shield shutter mechanism, whereby to provide a rapidly changing magnetic field; and
   a computerized controller for operating at least one of the movement mechanism and the magnetic shield shutter mechanism of at least one of the magnet assemblies so as to apply a rapidly changing magnetic field to the brain of the individual, wherein the computerized controller is configured to operate at least one of the movement mechanism and the magnetic shield shutter mechanism of the at least one of the magnet assemblies so as to provide intermittent oscillatory stimulation and, simultaneously, to operate at least one of the movement mechanism and the magnetic shield shutter mechanism of at least one of the magnet assemblies so as to provide continuous oscillatory stimulation, whereby to induce weak electric currents in the brain of an individual so as to modify the natural electrical activity of the brain of the individual.

2. Apparatus according to claim 1 wherein the computerized controller operates at least one of the movement mechanism and the magnetic shield shutter mechanism of a plurality of the magnet assemblies in a coordinated fashion so as to induce the desired weak electric currents in the brain of an individual so as to modify the natural electrical activity of the brain of the individual.

3. Apparatus according to claim 1 wherein each of the magnet assemblies is configured to provide a rapidly changing magnetic field of at least 500-600 Tesla/second.

4. Apparatus according to claim 1 wherein the computerized controller is configured to provide intermittent oscillatory stimulation, wherein the rapidly changing magnetic field is applied for a stimulus period of a given duration, wherein the stimulus period has a repetition rate of a given frequency, and further wherein the stimulus periods are separated by periods of substantial quiet.

5. Apparatus according to claim 4 wherein the stimulus period has a duration of 1-500 ms.

6. Apparatus according to claim 4 wherein the stimulus period has a repetition rate of 0.1-10 Hz.

7. Apparatus according to claim 1 wherein the computerized controller is configured to provide continuous oscillatory stimulation, wherein the rapidly changing magnetic field is applied continuously throughout the duration of a stimulation session.

8. Apparatus according to claim 1 further comprising a plurality of electrodes for monitoring the electrical activity of the brain.

9. A method for providing Transcranial Magnetic Stimulation (TMS) to an individual, the method comprising:
providing apparatus comprising:
a head mount for disposition on the head of an individual;
a plurality of magnet assemblies for releasable mounting on the head mount, wherein each of the magnet assemblies comprises a permanent magnet, and at least one of (i) a movement mechanism for moving the permanent magnet and/or (ii) a magnetic shield shutter mechanism, whereby to provide a rapidly changing magnetic field; and
a computerized controller for operating at least one of the movement mechanism and the magnetic shield shutter mechanism of at least one of the magnet assemblies so as to apply a rapidly changing magnetic field to the brain of the individual, wherein the computerized controller is configured to operate at least one of the movement mechanism and the magnetic shield shutter mechanism of the at least one of the magnet assemblies so as to provide intermittent oscillatory stimulation and, simultaneously, to operate at least one of the movement mechanism and the magnetic shield shutter mechanism of at least one of the magnet assemblies so as to provide continuous oscillatory stimulation, whereby to induce weak electric currents in the brain of an individual so as to modify the natural electrical activity of the brain of the individual;
positioning the head mount on the head of the individual, and positioning a selected number of magnet assemblies on the head mount at selected locations; and
selectively providing a rapidly changing magnetic field with at least one of the magnet assemblies.

10. A method according to claim 9 wherein the computerized controller operates at least one of the movement mechanism and the magnetic shield shutter mechanism of a plurality of the magnet assemblies in a coordinated fashion so as to induce the desired weak electric currents in the brain of an individual so as to modify the natural electrical activity of the brain of the individual.

11. A method according to claim 9 wherein each of the magnet assemblies is configured to provide a rapidly changing magnetic field of at least 500-600 Tesla/second.

12. A method according to claim 9 wherein the computerized controller is configured to provide intermittent oscillatory stimulation, wherein the rapidly changing magnetic field is applied for a stimulus period of a given duration, wherein the stimulus period has a repetition rate of a given frequency, and further wherein the stimulus periods are separated by periods of substantial quiet.

13. A method according to claim 12 wherein the stimulus period has a duration of 1-500 ms.

14. A method according to claim 12 wherein the stimulus period has a repetition rate of 0.1-10 Hz.

15. A method according to claim 9 wherein the computerized controller is configured to provide continuous oscillatory stimulation, wherein the rapidly changing magnetic field is applied continuously throughout the duration of a stimulation session.

16. A method according to claim 9 further comprising a plurality of electrodes for monitoring the electrical activity of the brain.

* * * * *